United States Patent
Schulter et al.

(10) Patent No.: US 10,426,711 B2
(45) Date of Patent: Oct. 1, 2019

(54) DENTAL IMPLANT FRAMEWORK

(71) Applicant: Cagenix, Inc., Memphis, TN (US)

(72) Inventors: Drew Schulter, Memphis, TN (US);
Carl Schulter, Germantown, TN (US);
Kyle Fraysur, Cordova, TN (US);
Daryl Newman, Williston, TN (US);
Belal Hamadeh, Memphis, TN (US)

(*) Notice: Subject to any disclaimer, the term of this patent is extended or adjusted under 35 U.S.C. 154(b) by 513 days.

(21) Appl. No.: 14/272,566

(22) Filed: May 8, 2014

(65) Prior Publication Data
US 2015/0320520 A1 Nov. 12, 2015

(51) Int. Cl.
| | |
|---|---|
| *A61C 8/00* | (2006.01) |
| *A61K 6/04* | (2006.01) |
| *A61C 13/00* | (2006.01) |
| *A61C 9/00* | (2006.01) |
| *A61B 6/03* | (2006.01) |
| *A61C 13/34* | (2006.01) |
| *A61C 13/01* | (2006.01) |
| *A61C 5/77* | (2017.01) |
| *A61B 6/14* | (2006.01) |

(52) U.S. Cl.
CPC .............. *A61K 6/04* (2013.01); *A61B 6/032* (2013.01); *A61B 6/14* (2013.01); *A61C 5/77* (2017.02); *A61C 8/0027* (2013.01); *A61C 8/0048* (2013.01); *A61C 8/0054* (2013.01); *A61C 9/0053* (2013.01); *A61C 13/0004* (2013.01); *A61C 13/0006* (2013.01); *A61C 13/01* (2013.01); *A61C 13/34* (2013.01); *A61C 8/0001* (2013.01); *A61C 13/0013* (2013.01)

(58) Field of Classification Search
CPC . A61C 8/0027; A61C 8/0054; A61C 13/0004; A61C 5/10; A61C 13/0006; A61C 9/0053
USPC .................. 433/173, 213, 214, 218, 219
See application file for complete search history.

(56) References Cited

U.S. PATENT DOCUMENTS

| | | | |
|---|---|---|---|
| 4,663,720 A | 5/1987 | Duret | |
| 4,724,464 A | 5/1988 | Duret | |
| 5,401,170 A | 3/1995 | Nonomura | |
| 5,527,182 A * | 6/1996 | Willoughby | A61C 8/0001 433/172 |
| 5,562,448 A | 10/1996 | Mushabac | |
| 5,725,376 A | 3/1998 | Poirier | |
| 5,851,115 A | 12/1998 | Carlsson | |
| 5,857,853 A * | 1/1999 | van Nifterick | A61C 13/0004 433/173 |
| 5,873,721 A * | 2/1999 | Willoughby | A61C 8/0001 433/172 |
| 5,938,446 A | 8/1999 | Andersson | |
| 5,993,214 A | 11/1999 | Persson | |
| 6,261,098 B1 | 7/2001 | Persson | |
| 6,287,119 B1 | 9/2001 | van Nifterick | |
| 6,382,975 B1 | 5/2002 | Poirier | |
| 6,558,162 B1 * | 5/2003 | Porter | A61C 8/0001 433/173 |
| 6,788,986 B1 | 9/2004 | Traber | |
| 6,790,040 B2 | 9/2004 | Amber | |
| 6,814,575 B2 | 11/2004 | Poirier | |

(Continued)

*Primary Examiner* — Nicholas D Lucchesi
(74) *Attorney, Agent, or Firm* — David J. Kreher

(57) ABSTRACT

An improved method of a dental framework design and manufacturing, incorporating a dental framework design volume to eliminate framework or denture teeth modification post framework manufacturing.

42 Claims, 20 Drawing Sheets

(56) References Cited

U.S. PATENT DOCUMENTS

| | | |
|---|---|---|
| 6,835,066 B2 | 12/2004 | Iilyama |
| 6,925,198 B2 | 8/2005 | Scharlack |
| 7,020,325 B2 | 3/2006 | Park |
| 7,333,874 B2 | 2/2008 | Taub |
| 7,425,131 B2 | 9/2008 | Amber |
| 7,887,327 B2 * | 2/2011 | Marotta ................ A61C 1/084 433/213 |
| 8,425,229 B2 * | 4/2013 | Nilsson ............... G06F 19/3437 433/172 |
| 8,875,398 B2 | 11/2014 | Balshi |
| 2003/0020906 A1 | 1/2003 | Li |
| 2003/0219148 A1 | 11/2003 | Scharlack |
| 2004/0089962 A1 | 5/2004 | Valery |
| 2004/0106087 A1 | 6/2004 | Weigl |
| 2004/0166476 A1 * | 8/2004 | Weissman ........... A61C 8/0048 433/173 |
| 2005/0019728 A1 | 1/2005 | Rostagno |
| 2005/0037320 A1 | 2/2005 | Poirier |
| 2005/0089822 A1 | 4/2005 | Geng |
| 2005/0170311 A1 | 8/2005 | Tardieu |
| 2005/0186540 A1 | 8/2005 | Taub |
| 2006/0040236 A1 | 2/2006 | Schmitt |
| 2006/0072810 A1 | 4/2006 | Scharlack |
| 2006/0093988 A1 | 5/2006 | Swaelens |
| 2006/0105294 A1 | 5/2006 | Burger |
| 2006/0106484 A1 | 5/2006 | Saliger |
| 2006/0115793 A1 | 6/2006 | Kopelman |
| 2006/0122719 A1 | 6/2006 | Kopelman |
| 2007/0134625 A1 | 6/2007 | Leu |
| 2008/0131841 A1 | 6/2008 | Taub |
| 2008/0176188 A1 | 7/2008 | Holzner |
| 2009/0081618 A1 * | 3/2009 | LaMar ................ A61C 8/0048 433/218 |
| 2009/0104585 A1 * | 4/2009 | Diangelo ............ A61C 8/0001 433/223 |
| 2009/0325125 A1 * | 12/2009 | DiAngelo ........... A61C 8/0001 433/173 |
| 2011/0171604 A1 * | 7/2011 | Durbin ..................... A61O 5/08 433/213 |
| 2012/0088208 A1 * | 4/2012 | Schulter ............... A61C 8/0001 433/173 |
| 2012/0214121 A1 * | 8/2012 | Greenberg ........... A61B 5/0088 433/24 |
| 2012/0284000 A1 | 11/2012 | Nilsson |
| 2014/0051037 A1 * | 2/2014 | Fisker ................. A61C 8/0048 433/213 |
| 2014/0205969 A1 * | 7/2014 | Marlin ................ A61C 8/0001 433/173 |
| 2015/0164620 A1 * | 6/2015 | Berger ................ A61C 8/0068 433/173 |
| 2015/0250569 A1 * | 9/2015 | Frick ..................... A61C 8/005 433/202.1 |

\* cited by examiner

DENTAL IMPLANT FRAMEWORK

CROSS-REFERENCE TO RELATED APPLICATIONS

| 66,821,238 | May, 2013 | Schuler, et al. |
|---|---|---|
| 8,100,692 | January, 2012 | Diangelo, et al. |
| 11/576,450 | September, 2005 | Karlsson, Anders |

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC

Not Applicable

FIELD OF THE INVENTION

Dental prosthetics having individual crowns placed on top of a framework is becoming more popular due to improved aesthetics of individual crowns and the ability to replace and repair an individual crown when chipped, broken, or otherwise damaged as opposed to having to replace or repair the entire prosthesis as a unit. However, the process for the development of the framework has several challenges, namely that it only utilizes a portion of the spatial dimensions of a patient's mouth, it requires technicians to purchase copings and screws to generate, and is extremely time intensive. A need exists for a method in which one can easily and readily identify the correct position and orientation of the crown copings and minimize the trial and error process and rework currently needed to produce an individual crown dental prosthetic.

Background of the Invention

Current individual crown prosthetics are fabricated by a process, herein referred to as the "copymill" process, where an acrylic pattern of the framework is first fabricated, then duplicated in titanium or another material. This process has several challenges, namely that it only utilizes a portion of the spatial dimensions of a patient's mouth, it requires technicians to purchase copings and screws to generate, and is extremely time intensive.

The current "copymill" process will begin in very much the same way that a traditional cast framework is created. The dentist or technician will create a stone cast and diagnostic wax up from the impression and clinical measurements taken at the time of the impression. Implant analogs will be included in the stone cast providing replicas of the implant and/or abutment mating geometries found in the patient's mouth. The diagnostic wax up will provide the appropriate position of the denture teeth that will be incorporated into the design of the final prosthesis. Once the denture teeth positions have been deemed acceptable by the patient and doctor, the technician will create a facial index of the denture tooth set up. Utilizing this facial index as a guide, the technician will attach a series of copings to the implant analogs and utilizing either wax or an acrylic material begin fashioning by hand the design of the framework to support the individual crowns. The technician is somewhat limited in designing the individual crown framework as he/she only has the facial boundary of the diagnostic wax up to utilize as a guide. The technician will be extremely limited in being able to visualize the correct position of the framework in the occlusal and lingual dimensions for the case. There will also be limits in determining the position of the margins where each individual crown will mate with the framework. This process requires a highly skilled technician who will have to utilize his/her experience and talent in order to appropriately fashion an acceptable design.

Once the wax/acrylic pattern of the individual crown framework has been generated, the technician can choose to either cast the framework or submit the wax/acrylic pattern to a milling company who will duplicate the design by milling the structure out of a single piece of titanium. This duplication milling process is commonly termed "copymill".

The casting technology traditionally used in fabricating the framework is fraught with errors and usually results in the framework having to be cut and soldered in order to properly mate with the implants in the patient's mouth. This cutting and soldering process results in additional visits for the patient and weakens the overall strength and integrity of the framework.

The copymill process provides improvements to the fit of the individual crown framework to the implants in the patient's mouth, but there are limits associated with tool access in cutting many of the finer geometries the dental technician incorporated in the design of the framework. During the manufacturing process of the copymill individual crown framework, there will be radiuses, tool marks, and additional material left over due to the limits of the tool diameter or tool access. These radiuses, tool marks, and additional material will have to be removed by hand by the technician. This issue of excess material is especially problematic in dealing with the margins where the individual crowns will mate to the framework. Refining the milled framework is once again an extremely time intensive task requiring a highly trained technician.

Once the framework has been checked for fit, refined, and deemed acceptable by both the doctor and technician, the individual crowns can be fabricated. An impression of the framework on the stone cast is taken and a new stone cast of the framework is made. The stone cast of the framework is pinned, based, and sectioned to allow for each of the individual support posts and margins that will support the crowns to be scanned. The technician will refine the margin for each individual support post by hand and provide a clear delineation which can be captured by the scanner. Once all of the margins have been refined, the technician will scan the stone cast of the framework with all of the individual support posts appropriately placed along with the opposing arch. The technician will then scan each individual support post separately and define the location of the margin. From this point, the technician can begin designing each individual crown on the basis of the opposing dentition. Once all of the crowns have been designed, the technician can load the design file into a milling machine where they can be fabricated from several different materials (i.e. Zirconia, Wax, Titanium, etc. . . . ). The technician can also use a number of other manufacturing processes in addition to milling, such as 3D Printing, Laser Sintering, Ceramic Pressing, Casting or EDM.

The manufactured crowns are then assessed for their fit against the copymill individual crown framework. Sometimes slight modifications/adjustments will have to be made to ensure the crown has the appropriate passive fit relative to the margin. The crowns are also checked for appropriate occlusion against the opposing arch. At this point, the technician or dentist may choose to perform a framework try in, where the framework and crowns are placed on the implants in the patient's mouth and the design is reviewed by the dentist and patient. Depending upon any critiques from the patient, the technician may need to adjust portions of the framework or crowns to accommodate these aesthetic demands.

Finally the framework and crowns can be finished with applying the appropriate acrylic or porcelain materials for the pink gingiva and the crowns can be stained glazed or have porcelain added to provide the appropriate aesthetic finish.

One can appreciate the time, skill, and potential rework associated with this process in order to achieve an acceptable framework with crowns that meet the clinical needs of the dentist and aesthetic demands of the patient. A need exists for a method in which one can easily and readily identify the correct position and orientation of the crown copings and minimize the trial and error process and rework currently needed to produce an individual crown dental prosthetic.

In U.S. Provisional Patent Application 66/821,238 Schulter et al. claims an "Individual Crown Dental Framework Method and Prosthesis," for which this application claims the benefit.

In U.S. Pat. No. 8,100,692 Diagenlo, et al., teaches a dental framework that is attached to dental anchors, such as dental implants which are secured to the patient's mandible or maxilla, where the framework may be fabricated based on the dimensions and surface contours of a stone cast and diagnostic wax up created from an impression of the patient's mouth.

In U.S. patent application Ser. No. 11/876,450 Karlsson teaches of the utilization of a dental scanning unit commonly found in the market place.

SUMMARY OF THE INVENTION

In accordance with the first embodiment of the invention, a dental prosthesis is disclosed consisting of a dental implant framework and series of crowns that are intended to mate with a series of implants and abutments in a patient's mouth and reestablish the patient's loss dentition. The crowns are a part of an assembly consisting of a crown and support post and consist of known dimensions. The support post possesses a margin where the crown will ultimately mate. These assemblies are aligned in a proper orientation to replace the patient's missing dentition and are easily editable to provide flexibility at the time of design in meeting any clinical or aesthetic demands of the patient. Bridging structures are used in connecting the support posts and the fittings that will mate with the implants and abutments. The combination of bridging structures, support posts, and fittings will provide the completed design of the dental implant framework. The crowns can be combined together into a bridge and even have gingiva contours added per the discretion of the operator. As the dimensions of the crown and support post assemblies are known, the dental implant framework and crowns (bridges, if preferable) can be designed and manufactured simultaneously.

In accordance with a second embodiment of the invention, a method for designing a dental implant framework and series of crowns is provided. Through the use of digital data the location and orientation of the proposed position of the crowns is determined. A second set of digital data is used in identifying the location of the implants and abutments in the patient's mouth. On the basis of these digital data sets fittings and crown/support post assemblies are aligned appropriately and provide the basis for designing the dental implant framework and crowns for the dental prosthesis. The design of the crowns and dental implant framework are conducted simultaneously and the resulting CAD models are used in fabricating the crowns and dental implant framework out of the preferred material and manufacturing methodology. Gingival contours can be applied to the dental implant framework and crowns by means of acrylic, composite, porcelain, or another preferred material being processed to the dental implant framework and crowns. The gingival contours can also be incorporated into the design of the dental implant framework and crowns and manufactured at the same time as the dental implant framework and crowns.

In accordance with the third embodiment of the invention, a CAD library of crowns and support posts is disclosed. This CAD library and crowns is used in the design process in fabricating a dental implant framework and series of crowns for a dental prosthesis. The crowns and support posts of the CAD library can be based on the dimensions of the teeth that they are intended to be replaced. They can also be based on denture teeth that are commonly available in the market place or on the basis of crown and tooth libraries commonly found in many of the design software systems available in the market. The crown and support post models are completely parametric and dependent upon one another, where edits can be easily made to these models per the clinical aesthetic demands of the patient and changes in features of one will result in automatic updating of the second dependent body. This crown and support post CAD library provides one with a rapid design process for the fabrication of a dental implant framework and crowns for a dental prosthesis.

DETAILED DESCRIPTION OF THE INVENTION

The dental prosthesis is supported by a dental framework which functions as a structural support and point of attachment. The dental framework is attached to dental anchors, such as dental implants which are secured to the patient's mandible or maxilla, the framework may be fabricated based on the dimensions and surface contours of a stone cast and diagnostic wax up created from an impression of the patient's mouth such as described in U.S. Pat. No. 8,100, 692. The stone cast replicates the soft tissue contours and implant positions in the patient's mouth. The diagnostic wax up represents the final prosthesis and ultimately the position of the denture teeth to be restored for the patient. In order to create the diagnostic wax up, the dentist or technician will position upon the stone cast the stock denture teeth and wax as required for proper prosthetic function and aesthetics. The commercially available stock teeth are generally manufactured with predetermined geometries of a typical given tooth in various sizes by a third-party manufacturer.

Figure 1:
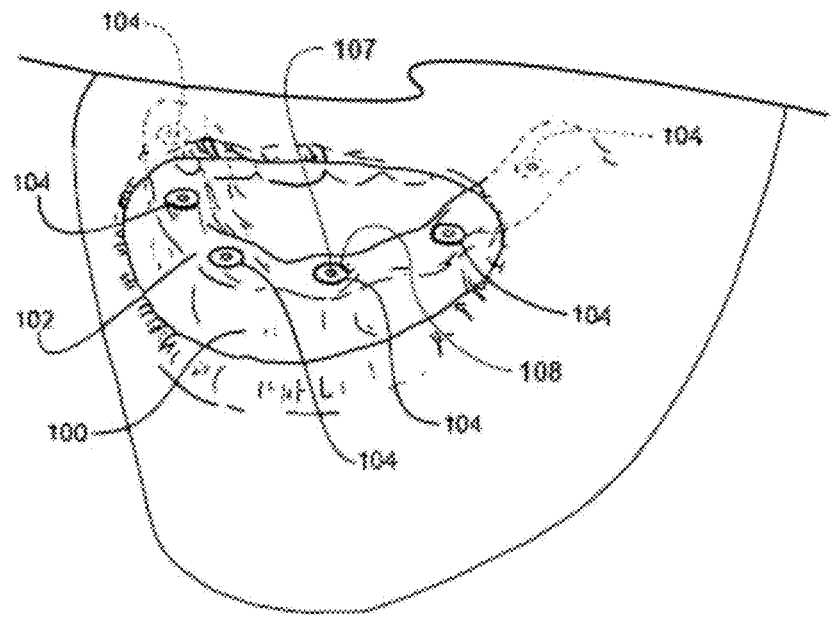
FIG. 1 is a fragmentary perspective view of a patient's open mouth with the anchors embedded in the patient's mandible.

Retention of the dental prosthetic requires anchors secured in the patient's mouth. In FIG. 1, the patient's jaw or mandible 100 can be seen overlaid with soft mucosal tissue 102 (known commonly as "gum tissue"). An anchor 104, also known as an "implant" or "fixture" is shown embedded into the patient's mandible 100. This anchor is retained within the bone of the mandible by a screw thread. It is driven into the mandible 100 by coupling a wrench or similar device to the top of the anchor 104 and rotating the wrench to drive the anchor into the jaw bone just as one would drive a screw into a piece of wood. In an alternative embodiment, the anchor 104 is press fitted into a hole formed with a drill, reamer, broach, osteotome, or similar device.

FIG. 1 illustrates the first step in the process, that of forming an opening in the mandible of the patient and fixing an anchor therein, while leaving a top surface of the anchor exposed above mucosal tissue 102 for mating (coupling) to and supporting a dental prosthesis or restorative component such as a denture, bridge, crown, framework, abutment, healing cap, or coping (hereinafter referred to as "denture"). Note that while the process illustrated herein describes and illustrates a mandible for illustration purposes, the same process is performed to embed anchors 104 into the patient's maxilla and create dental prostheses for the maxilla.

To attach anchors 104, the dentist first makes an incision in the mucosal tissue 102 where a missing tooth or teeth would normally extend from the mandible where it is embedded, through the gum, and into the oral cavity. Once the incision is made, the dentist makes a hole (which may include such processes as drilling, broaching or reaming) in the mandible 100 in the same general direction and location as the missing tooth. The dentist then fixes an anchor 104 into the hole thus created and sutures the incision, typically leaving mating surface 108 of anchor 104 exposed while the bone osseointegrates to the outer surface of anchor 104. Alternatively, the dentist may attach a healing cap to the anchor 104 and suture the gum around or over the top of the anchor 104 and the healing cap, permitting the gum to heal around or over the top of the anchor 104 as it osseointegrates. In this alternative process, once the anchor has osseointegrated, the dentist incises the mucosal tissue 102 extending over the top of the now-integrated anchor 104 and retracts the mucosal tissue to each side, exposing the mating surface 108 of anchor 104 and permitting the mucosal tissue to heal.

Figure 2:
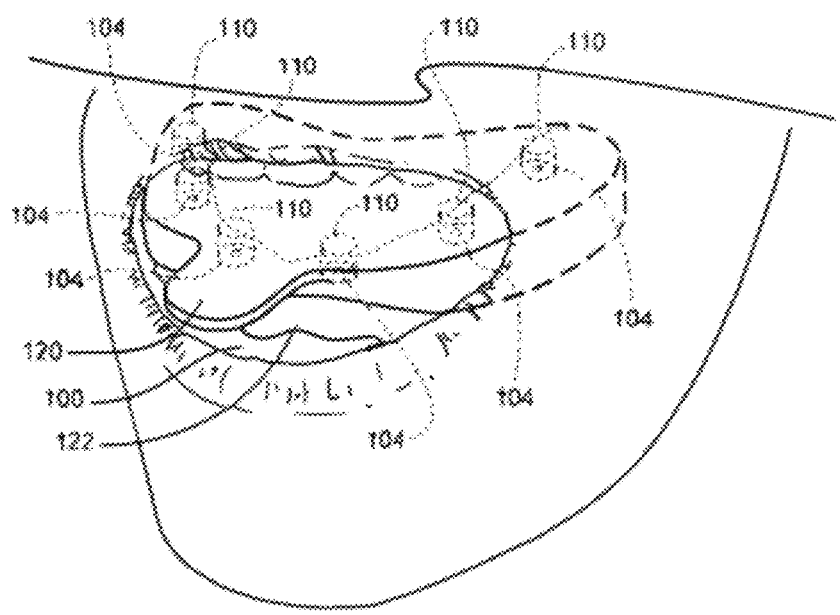
FIG. 2 is a fragmentary perspective view of the patient's open mouth with several copings attached to the anchors and an impression tray with impression material surrounding the patient's mucosal tissue and submerging the copings.

The anchor 104 has a central longitudinal aperture 107 in the top which is configured to receive an impression coping 110, as shown in FIG. 2, (or a fastener configured to mount the impression coping 110) that is affixed to the anchor 104. This coping transfers the size, shape, location or orientation of the mating surface 108 of the anchor (and preferably all four) to the stone cast (see below). It is the mating surface 108 that is oriented to the finished denture, and hence the mating surface 108 from which the structures of the denture that mount to the anchors are derived. In general, anywhere from one to twelve of these anchors are embedded in the jaw and are provided as mounting points for the denture. In an alternative configuration, anchor 104 may have a variety of configurations on its mating surface 108 including threaded or unthreaded protrusions or recesses that are configured to engage a denture. The use of an anchor 104 having a central aperture and internal threads for engaging a coping is a matter of convenience herein and should not suggest that the process is limited to an anchor having this configuration.

Mating surface 108 is typically the surface on which the denture will be mounted or a surface having a predetermined position with respect to that surface on which the denture will ultimately be mounted. The coping 110 is configured to engage surface 108 and surrounding structures of anchor 104 (if any) such as holes that extend into (or protrusions that extend above) the surface 108.

These inter engaging surfaces of coping 110 and anchor 104 serve to align the coping and the anchor in predetermined positions with respect to each other when fixed together, such that if one knows the position and orientation of surfaces on the coping one can know the position and orientation of corresponding structures on the anchor 104 and more preferably when a scanner (see below) determines the position and orientation of structures on copings 110 it can mathematically determine the position and orientation of corresponding structures on anchors 104. Anchor 104 is preferably cylindrical and has a longitudinal axis 111, as does coping 110. In a typical arrangement, when the coping 110 is fixed in its predetermined position with respect to anchor 104, a longitudinal axis 111 of the coping is coaxial with the longitudinal axis of the anchor 104. The coping 110 and the anchor 104 are preferably threadedly engaged to permit surfaces on the coping to be drawn down tightly against mating surface 108 for precise alignment of their inter engaging surfaces. Alternatively, the coping 110 and anchor 104 to which it is coupled may be equipped with inter engaging snap fastening connecting surfaces that hold the coping in the proper orientation with respect to anchor 104.

In FIG. 1, the edentulous mandible 100 has six anchors 104 affixed therein in a spaced-apart relation extending from the front of mandible 100 around each side. The anchors 104 are disposed in a generally upright and parallel relation extending into the top surface of mandible 100. The dentist attaches corresponding copings 110 to the top of each anchor 104 and extends upward in a generally upright and parallel relation to the other copings 110. The application illustrated herein shows the use of six anchors configured to support a denture. Other applications with more or fewer anchors 104 are possible. Furthermore, the mandible need not be edentulous (shown here), but may have, and often does have, one or more natural teeth remaining in the maxilla or mandible between which the anchors 104 are embedded to support one or more dentures (such as fixed or removable partial dentures) to fill the gap or gaps between the existing natural teeth. In this case, the anchors would not be spaced evenly about the mandible, as shown here, but would be spaced irregularly in the gaps created by the absence of natural teeth.

FIG. 2 illustrates the next step in the process of creating a denture, the step of creating an impression of the patient's mandible. This figure shows an impression tray 120 filled with flexible impression material 122. The tray is a semi flexible plastic structure that holds the impression material 122 in position around the patient's teeth (if any) and mucosal tissue. FIG. 2 shows a tray 120 for the lower teeth surrounding teeth, mucosal tissue, and mandible of the patient.

The copings 110 previously attached by the dentist to the anchors 104 are completely submerged by the dentist in impression material 122 such that the entire outer surfaces of the copings 110 extending above the surface of the mucosal tissue on the patient's mandible 100 are completely covered. The impression material is left in this position to set. Once set, the individual copings 110 are fixed with respect to each other in the same position and orientation that the anchors 104 are fixed with respect to each other. The curing process fixes the copings in this position and thereby permits the copings to be collectively removed together with the impression material while preserving their orientation.

In the next step of the process, the dentist flexes the tray 120 and the now set impression material 122 and removes them from the patient's mouth. Enough impression material 122 is placed in the tray and disposed around the patient's mandible 100 to cover any still-existing teeth of the mandible and the mucosal tissue 102 of the mandible as well as the copings 110.

When the tray 120 and impression material 122 are removed, the copings are removed with them, embedded in the now-cured impression material 122. The process of removal disconnects the copings 110 from the anchors 104, permitting the copings to be removed while still embedded in the impression material 122. If the copings include a threaded portion that holds them to the anchors, this threaded portion is unthreaded from the anchors. If the copings are fastened to the anchors with a snap fastening portion, the snap fastening portions are unsnapped from each other. The now-cured impression material 122 that couples the copings 110 to each other preserves the relative positions and orientations of the mating surfaces of all the copings 110 and hence relative positions and orientations of the mating surfaces 108 of all the anchors 104 with respect to each other. This relationship is preserved in the relative positions and orientations of the surfaces of copings 110 that were connected to the mating surfaces 108 of anchors 104. To even further ensure the preservation of this relationship, some dentists will attach the copings 110 to one another by applying a light cured acrylic material prior to submerging them in the impression material 122. The impression material 122 in which copings 110 are embedded also preserves the surface contours of the mucosal tissue and the remaining teeth (if any) in the mandible and their relative positions with respect to the mating surfaces of copings 110 and anchors 104. The surface of the impression material 122, once removed from the patient's mouth, is a negative replica of the soft tissue and teeth. The surfaces of copings 110, now separated from anchors 104 and exposed on the inside surface of the impression material 122, are a negative replica of surfaces 108 of anchors 104 to which they were coupled. The now-cured impression material 122 is therefore a negative replica of all the free surfaces, including teeth, mucosal tissue, and the surfaces of the copings embedded in the impression material are a negative replica of the mating surfaces 108 of anchors 104. The cured impression material with embedded copings is commonly called an "impression" and identified in the figures herein as item 123.

Figure 3:
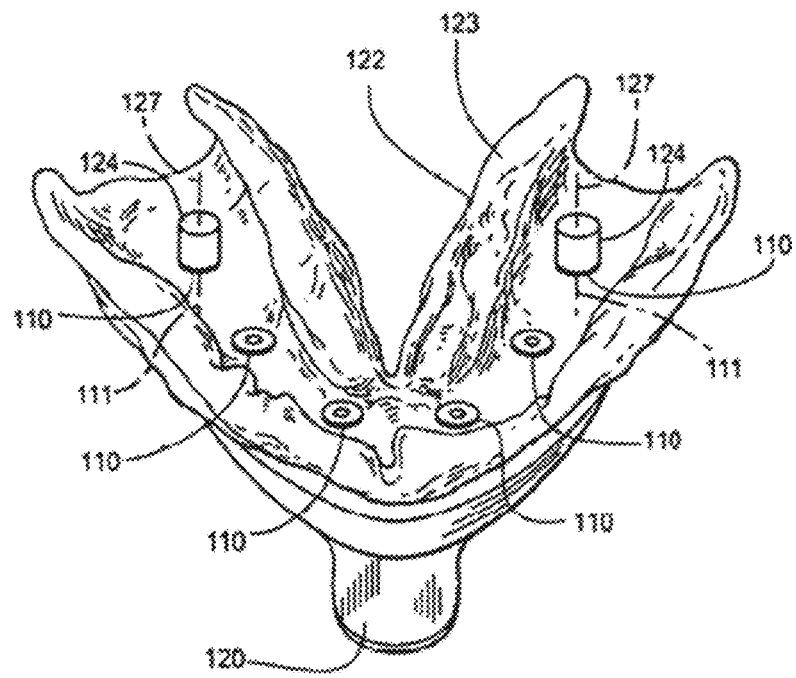
FIG. 3 is a perspective view of the impression of FIG. 2 inverted and removed from the patient's mouth with two analogs attached to two of the copings.

FIG. 3 shows the impression 123 inverted and removed from the patient's mouth. In this embodiment, there are six copings 110 embedded in the impression 123. The bulk of the copings 110 are embedded in the impression 123. Only the very ends of the copings 110 extend upward and out of the impression 123 (in this inverted orientation).

In FIG. 3 the dentist has begun the next step of the process, that of attaching analogs 124 to the exposed surfaces of all of the copings 110. Analogs 124 are structures that replicate the anchors 104. As in the case of the copings themselves, each analog 124 preferably comprises a generally cylindrical body with a longitudinal axis 127 that is coaxial with the longitudinal axis 111 when attached to coping 110.

The end surfaces of analogs 124 are configured to abut and mate with the free surfaces of the copings 110 that were previously coupled to anchors 104 and normally attach in the same manner as copings 110 to anchors 104. The surfaces of analogs 124 replicate the position and orientation of mating surfaces 108 of anchors 104. In effect, the spacing and orientation of anchors 104 was transferred to the copings 110, and transferred back again to analogs 124, which have the same spacing and orientation as the anchors 104. Thus, each analog 124 is coaxial with and is disposed in the same position as anchor 104.

Figure 4:
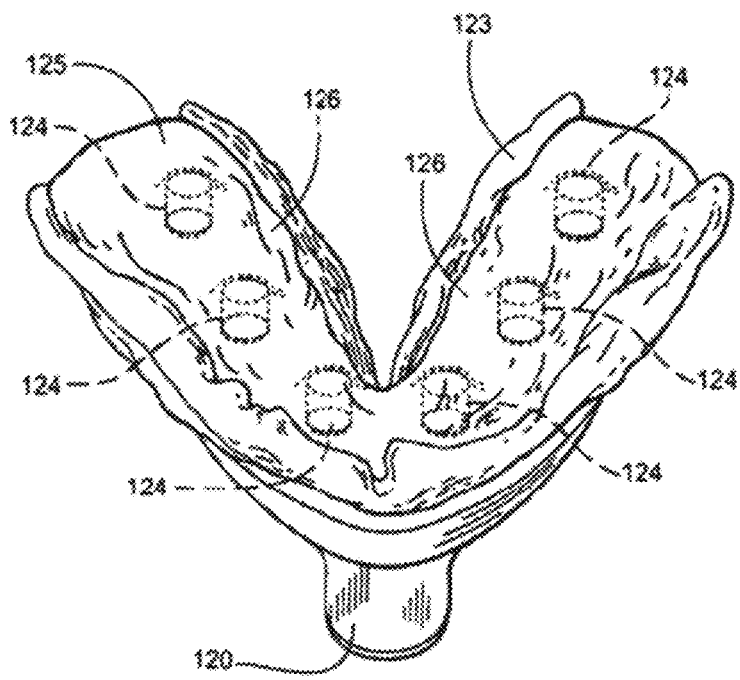
FIG. 4 is the same perspective view of FIG. 3, but with analogs attached to all the copings, and the impression filled with dental stone material and the analogs submerged in the dental stone material.

In the next step of the process, illustrated in FIG. 4, the dentist pours a mixed dental stone material 126 into the cavity in impression 123 that was formed by the patient's mandible, submerging all of the analogs 124. Stone material 126 covers the exposed portion of the analogs 124 as well as the surfaces of impression 123 formed by the patient's mucosal tissues and teeth. Once filled into impression 123, the stone material 126 is then permitted to harden to a rock-like consistency, creating a structure that is called a "stone cast" 125.

Figure 5:
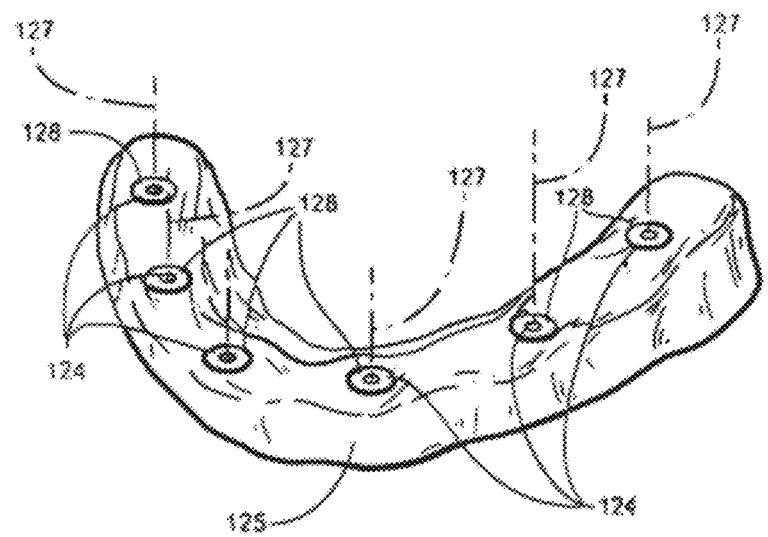
FIG. 5 is a perspective view of the stone cast formed by the dental stone material poured in the impression of FIG. 4 in its hardened state, inverted, and with the impression removed showing the analogs with the analog surfaces that mated with the copings (in FIG. 4) now exposed.

FIG. 5 represents the next step of the process which the dentist performs once the stone material 126 has hardened. The dentist removes impression 123 from the stone cast 125, leaving the stone cast 125 with the analogs embedded therein. The stone cast 125 positively replicates the position and orientation of mating surfaces 108 of anchors 104, which are represented in the stone cast 125 by the mating surfaces 128 of the analogs 124 that were fixed to the free ends of copings 110 (FIG. 3). The portions of the stone cast 125 surrounding analogs 124 positively replicates the surface of the mucosal tissues of the mouth, which were transferred from the mucosal tissues of the mouth to the impression as a negative replica and then back to the stone cast as a positive replica of those tissues. The stone cast 125 also replicates the surface of the patient's existing teeth (not shown). When the patient has existing teeth, the position and orientation of the surfaces of the teeth are transferred first to the impression as a negative replica and then to the stone cast as a positive replica. In the present embodiment, the mandible 100 is edentulous and therefore there are no existing teeth.

As will be explained later, teeth that are replicated in impression 123 and stone cast 125 provide a precise reference to indicate the location of the jawbone. The soft tissues that are replicated in the impression 123 and stone cast 125 can change their position due to swelling, edema, injury, irritation, or damage to the mouth. Teeth, since they are much harder and are embedded in the jawbone, provide a more stable reference, over time, of the position of the jawbone and thus indirectly, of the position and orientation of anchors 104.

The impression molding and stone casting processes described above provide accurate replicas of the position and orientation of the mating surfaces 108 of anchors 104, the mucosal tissues, and the teeth.

In the preferred embodiment, the mating surfaces 108 of anchors 104 are exactly duplicated by the mating surfaces 128 of the analogs 124: they are in exactly the same position and at exactly the same orientation. In an alternative embodiment, the mating surfaces 128 on the analogs may be offset slightly or configured slightly differently than the mating surfaces 108 of anchors 104. In some cases, manufacturers choose to make analogs or other connecting components that have mating surfaces slightly different from the mating surfaces 108 of the anchors 104 for example to permit the copings 110 to be more easily attached to anchors 104 or to permit analogs 124 to be more easily attached to copings 110. Any slight difference in position such as this is intentional, however, and is eliminated later in the process when the denture is created so that the mating surfaces of the denture are precisely oriented to mate properly with surfaces 108 of anchors 104 in the patient's mouth.

Further, the anchors 104 in the patient's mouth may not be connected directly to the dental framework. Abutments may be mounted on the anchors 104 (i.e. the anchors have surmounted abutments). The dental framework may be mounted to these abutments, and thus indirectly mounted to anchors 104. When the dental framework being designed is intended to be mounted on abutments mounted on anchors 104, the analogs 124 may be provided with surmounted abutments, i.e. the analogs may include the abutment design incorporated into it, to replicate the mating structure of the abutment to the framework.

While the mating surfaces 128 of the analogs 124 and the mating surfaces 108 of anchors 104 may be slightly differently configured, the longitudinal axes of each of the anchors 104 and the analogs 124 are preferably identically oriented and spaced apart, each pair of corresponding analog and anchor sharing a common longitudinal axis (i.e. they are coaxial). Considered differently, if the surface of the stone cast representing the soft tissues and teeth of the patient's mouth could be superimposed on top of the patient's mucosal tissues 108 that formed the stone cast 125, all the longitudinal axes defined by the analogs would be superimposed on (i.e. simultaneously coaxial with) all the corresponding axes defined by the anchors. The longitudinal axes 127 of the analogs 124 and the surfaces of the stone cast 125 defined by the mucosal tissues 108 the patient are positive replicas of the longitudinal axes 111 of anchors 104 and the surfaces of mucosal tissues 108.

The replica of any teeth formed in the surface of the stone cast are formed with respect to one another and with respect to the analogs such that they duplicate the position of any existing real teeth in the patient's mouth with respect to one another and with respect to mating surfaces 108 and longitudinal axes of the anchors 104 in the patient's mandible. The replica of the mucosal tissues formed in the surface of the stone cast are in generally the same position on the stone cast as they are in the patient's mouth including the replication in the stone cast 125 of the junction between the mucosal tissue and any existing teeth and anchors 104, as well as a replication in the stone cast of all the mucosal tissue that will be covered by the denture.

Once the dentist has created the stone cast 125, which is a positive replica of the patient's jaw, including replication of existing teeth, mucosal tissue, and anchors, the dentist then proceeds to the next step in the process: designing and creating the denture that will be fitted to the patient's mouth (in this case, the patient's jaw).

The dentist or technician manually creates a diagnostic wax-up 130 of the desired denture teeth position and occlusal orientation, using flexible molding materials such as wax, acrylic, or other polymers and stock denture teeth commonly found in the market. These stock denture teeth are of a known dimension and have contours specific to the mold or catalog number of the denture teeth. The dentist or technician may also modify these denture teeth slightly in order to provide the appropriate occlusal scheme to best fit any existing teeth or dental prosthesis on the opposing arch. These modifications may include but are not limited to the addition of occlusal contours by adding wax or the removal of occlusal contours by modifying the surface with a bur and hand piece.

The diagnostic wax-up 130 is created to verify the proper location of the denture mucosal tissue and denture teeth with respect to the patient's actual mouth to ensure proper tooth orientation, and to ensure that the location and placement of the denture within the patient's mouth restores form, fit and function. In short, the diagnostic wax-up 130 is a model of and looks like the denture that is ultimately produced, but is made of softer materials to permit it to be adjusted and adapted until the patient and dentist are pleased with its form, fit, function and aesthetics.

The dentist creates the wax-up 130 on the stone cast 125, building it up on the patient's replica mucosal tissue. When the dentist is finished making the wax-up 130, he removes the wax-up 130 from the stone cast 125, and places it into the patient's mouth so the patient can see, firsthand, what the denture or prosthesis will look like when it is finished. If the wax-up 130 fits, the patient can bite properly, and the patient is pleased with the appearance of the wax-up 130, the dentist then proceeds to manufacture the framework and resulting prosthesis.

Figure 6:
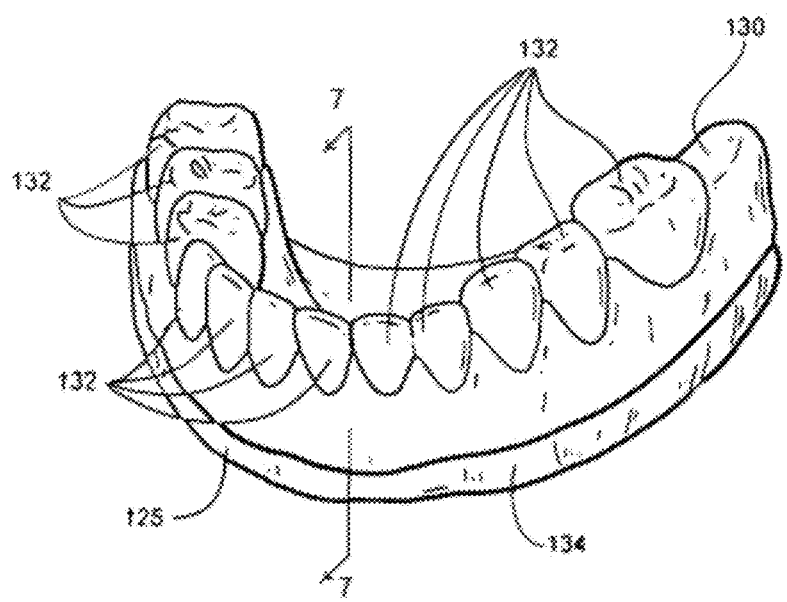
FIG. 6 is a perspective view of the stone cast of FIG. 5 with the dentist's fabricated diagnostic wax-up built up on the stone cast and abutting the analogs.
Figure 7:
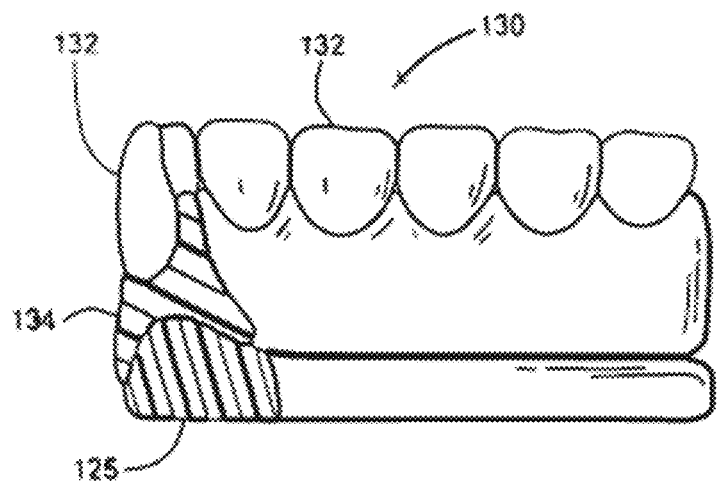
FIG. 7 is a cross-sectional view of the stone cast of FIG. 6 taken at section line 7-7 in FIG. 6.

FIGS. 6-7 illustrate the process of creating a wax-up, showing the stone cast 125 as it would appear with a wax-up 130 modeled on its outer surface. In FIG. 6, the stone cast 125 is shown covered with the wax-up 130 which comprises the denture teeth 132 embedded in wax 134 which the dentist has molded directly to the surface of the stone cast 125. FIG. 7 is a cross-sectional view through the stone cast 125 plus wax-up 130 shown in FIG. 6. This cross-section is taken at section line 7-7 in FIG. 6. Once the dentist has created the wax-up 130 and has verified the fitting of the wax-up 130 in the patient's mouth, he can then begin the process of having the individual crown framework fabricated for the patient.

Figure 8:
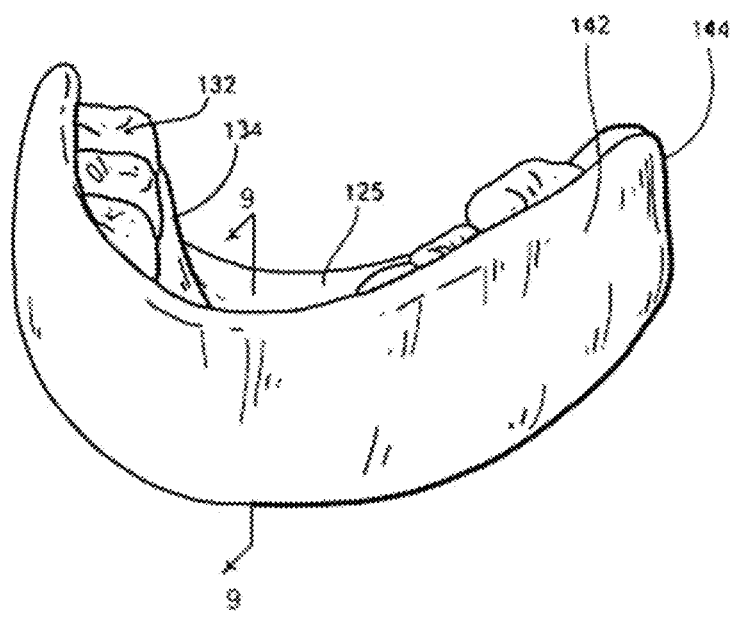
FIG. 8 is a perspective view of the stone cast of FIGS. 5-7, with a putty index molded to the facial aspect of the diagnostic wax-up.
Figure 9A:
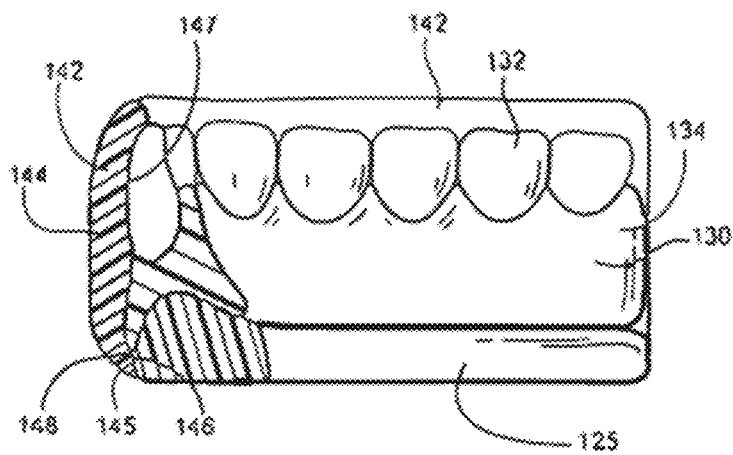
FIG. 9A is a cross sectional view of the stone cast of FIGS. 5-8 taken at section line 9-9 in FIG. 8.
Figure 9B:
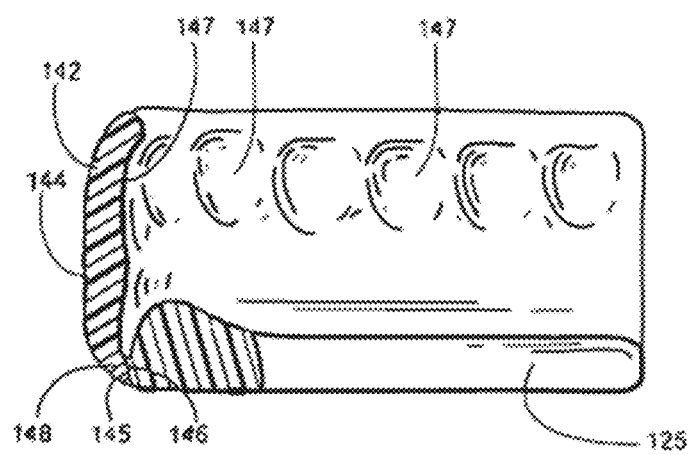
FIG. 9B is a cross sectional view of the stone cast of FIGS. 5-8 with the diagnostic wax-up removed to show the inner surface of the putty index and the impression of the facial aspect of the diagnostic wax-up formed on the inner surface of the putty index.
Figure 10A:
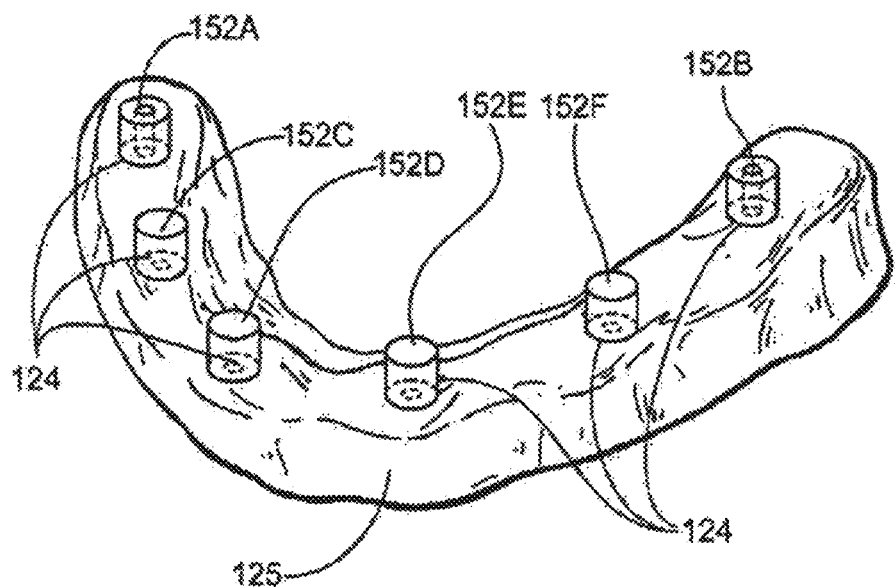
FIG. 10A is a perspective view of the stone cast of FIGS. 5-9B with six fittings, one fitting attached to each of the six analogs.
Figure 10B:
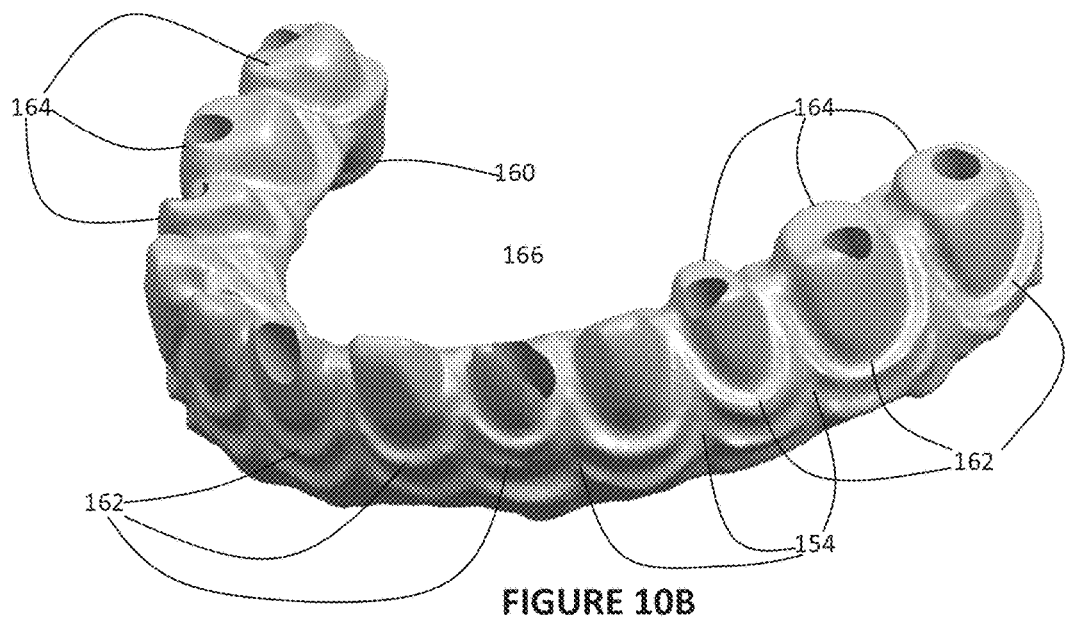
FIG. 10B is a perspective view of the bridging structures fixed to and between each of the six fittings to form a wax-up framework mounted on the six analogs.
Figure 11:
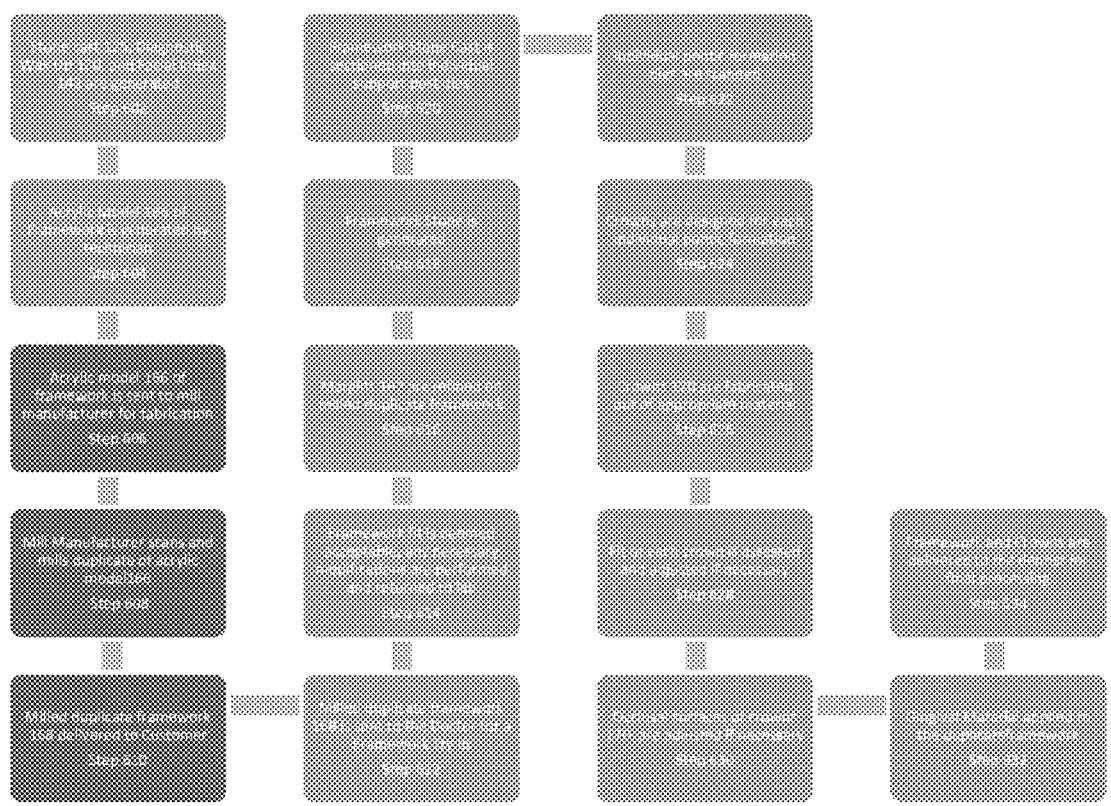
FIG. 11 is a flow chart demonstrating the steps necessary for fabricating a framework to receive individual crowns through a "copymill" procedure.

The steps associated with the traditional "copymill" process are outline in flowchart 600 of FIG. 11. As noted in STEP 604 of Flowchart 600, the Dentist or technician will begin to fabricate an acrylic model of the framework that will be duplicated in a material such as titanium, cobalt chrome, zirconia, or any other appropriate dental material. The first step in this process is creating a facial or putty index of the diagnostic wax-up 130 while positioned on stone cast 125, which captures the facial/buccal contours of the denture teeth 132 including their height and angulation and the soft tissue contours of the diagnostic wax up. FIGS. 8 and 9A-B illustrate the process of creating the facial index. FIG. 8 shows the facial index 142 as created using stone cast 125 and diagnostic wax up 130. This facial index 142 is created by wrapping a silicone putty material 144 commonly used in the dental industry around the facial/buccal aspect of the diagnostic wax up 130 while it is properly positioned on stone cast 125. The facial index will engage a significant area of the stone cast 125 that is not covered by diagnostic wax up 130. The facial index 142 will have a unique stone mating area 145 that will allow for the facial index to be properly positioned back to stone cast 125 without the aid of diagnostic wax up 130. FIG. 9A is a cross-sectional view through the facial index 142, stone cast 125, and diagnostic wax up 130, demonstrating the capturing of the buccal aspect of denture teeth 132. This cross-section is taken at section line 9-9 in FIG. 8. Once the putty material 144 has set the facial index 142 and diagnostic wax-up 130 can be removed from the stone cast 125. FIG. 9B shows the negative impressions 147 left by the facial/buccal contours of denture teeth 132. The facial index 142 will be placed back onto the stone cast 125 utilizing the unique stone mating areas 145. The dentist or technician will utilize facial index 142 as a guide to begin building the acrylic model of the intended framework. As demonstrated in FIG. 10A, wax copings or fittings 152A-F will be attached to the mating surface of the analogs 124 and begin stacking acrylic material 160 on top of them to begin forming the design. The acrylic material 160 can be a light cured or cold cured resin commonly used in dentistry. It can also be appreciated that materials other than acrylic such as wax can be used in creating the design of the framework by the dentist or technician. Frequently the dentist of technician will utilize a hand piece and bur to reduce and refine the contour of the acrylic material 160 in order to create the necessary margins 162 and support posts 164 that the individual crowns will be intended to mate to on the framework. As shown in FIG. 10B, the support posts 164 will be attached to one another by bridging structure 154 that will run between fittings 152. The inventor is using the term support posts as a descriptive term in this application, but others may refer to this framework feature as a pontic, abutment, prep tooth form or framework abutment. The support posts 164 will be designed in such a way as to support a crown that will be designed to mate to the margin 162 as designed into the framework. Depending upon the tooth type, the design of the support post 164 will be adapted per the dentist or technician to support the crown against the expected occlusal forces of the patient.

Once the acrylic model 166 of the framework is deemed acceptable the dentist or technician will send the acrylic model 166 and stone cast 125 to a laboratory or framework supplier to have the acrylic model duplicated in the material of their choosing. These STEPS 606, 608, and 660 are noted in Flowchart 600 shown in FIG. 11. The laboratory or framework supplier will scan the stone cast 125 to determine the orientation and location of the mating surfaces of analogs 124 and scan the acrylic model 166 to capture the contours designed by the dentist or the technician. Once an appropriate rendering of the acrylic model 166 has been generated, a tool path will be generated for fabricating the framework out of the appropriate material. The laboratory or framework supplier can use a number of manufacturing methods, such as milling, 3D Printing, Laser Sintering, Ceramic Pressing, EDM (Electric Discharge Manufacturing), etc . . . , in a multitude of materials, such as titanium, zirconia, cobalt chrome, semi-precious metals, etc. . . . to fabricate the resulting framework. It can also be appreciated that the dentist or technician may also possess the scanning and/or fabrication equipment necessary to perform these tasks or a portion of these tasks internally within their own facility.

Once the acrylic model 166 of the framework has been duplicated in the appropriate material the duplicate framework 168 and stone cast 125 are returned to the dentist or technician. As noted in STEPS 662 and 664, the duplicate framework 168 is placed in the patient's mouth onto anchors 104 and reviewed for fit and to ensure the duplicate framework 168 has the appropriate contours necessary for the final prosthesis. The dentist and technician may choose to alter some of the contours of the framework to better accommodate the necessary function, aesthetics and phonetics of the patient. These alterations can vary from reducing the height of the support posts 164 or reducing a facial/buccal/lingual contour of bridging structure 154 to reduce the potential of the prosthesis from extending into the cheek or tongue. Some dentists and technicians may elect to skip these steps.

As noted in STEPS 666-630, the dentist or technician can begin fabricating the crowns. The process outlined here in is in utilization of dental scanning unit commonly found in the market place. More detailed information regarding this process can be found in patent application Ser. No. 11/576, 450. The following information will only briefly cover the necessary steps associated with this process to provide a general understanding and should not be considered a detailed outline for the different scan/design systems currently available in the dental market. It can also be appreciated that the crowns can be fabricated by alternative means such as a more traditional waxing and casting method. This enclosed process should only be considered as exemplary. In STEP 666, the dentist or technician will refine the margins 162 of the framework where the crowns will mate. Many times the manufacturing process used in creating the duplicate framework can leave tool marks or additional material in these small areas due to limitations of tool size, access, or limitations of the manufacturing process itself. Using a hand piece and bur, the dentist or technician will remove any material left by the manufacturing process to create a clear and uniform margin 162 around the support post 164. Once the margins have been refined appropriately, the framework while positioned on stone cast 125 will be impressed utilizing an impression material 122 and a second framework stone will be created with dental stone material 126. These processes are noted as STEPS 668 and 620 in Flowchart 600. The dentist or technician will section the stone support posts from one another by splitting the framework stone into multiple individual dies. The individual support post dies will be separately scanned to accurately capture the margin where the crown will mate to the framework. The support post dies will be scanned together and a stone cast of the opposing arch will be scanned in an appropriate orientation relative to the support post formations. These scan sets will be appropriately aligned relative to one another. A crown for each support post will be designed virtually. This process can take considerable time for the dentist or technician in creating the individual support post dies, scanning each one, and then in turn designing an appropriate crown. Once the virtual models of the crowns are complete, the models are typically loaded into a mill where the crowns are manufactured out of an appropriate material such as zirconia, titanium, semi-precious metal, lithium disilicate, etc. . . . . The crowns can also be manufactured by means of additional manufacturing processes, such as 3D Printing, Laser Sintering, Ceramic Pressing, EDM, etc. . . . . Once all of the crowns 170 have been fabricated their fit is assessed against the margin 162 and support posts 164 of duplicate framework 168, as noted in STEP 628. Many times the technician or dentists have to reduce or modify the contours of the framework or crown in order to achieve the appropriate fit. If the fit is deemed unacceptable, the dentist or technician may need to attempt at refabricating the crown, which may result in creating a new impression of the framework and repeating the tasks associated with fabricating the necessary crowns, STEPS 668-628. These errors and reworks can be costly, time consuming and prevent the final prosthesis from being completed in a timely manner. When all of the crowns have been deemed to fit appropriately to the duplicate framework 168, the dentist or technician will check the occlusal contacts of the crowns against the opposing dentition and modify utilizing a hand piece and bur to reduce the occlusal contours and provide the appropriate level of contact with the opposing arch. A gingival mask can be applied to the framework, which can be performed in several ways either by processing pink acrylic, stacking composite materials, or applying porcelain onto the duplicate framework 168. These processes are commonly known in the dental industry and will not be covered in great detail here in this application. Finally the dentist is ready to deliver the duplicate framework with the gingival mask and cement the crowns 170 onto the framework in the patient's mouth.

It can be appreciated the level of skill and hours associated in performing the tasks as outlined above. There are also multiple areas where the dentist or technician can make a mistake or an error in the process can occur, resulting in lost time and money.

The enclosed invention is a digitally designed framework intended to support a series of individual crowns or bridges based upon the digital information of the patient's soft tissue contours and the proposed position of the teeth for the final prosthesis. This application also encloses the invented process in how to design and manufacture a framework and the subsequent crowns based upon the digital information of the patient's soft tissue contours and proposed position of the teeth for the final prosthesis. The final invention of the application is a library of crowns and support posts (also referred to as prep tooth forms or PTF's by the inventor) that are appropriately aligned to one another and possess dependent CAD features allowing for particular attributes and features to be updated automatically on the basis of changes to one features of either the crown or the prep tooth form.

The goal of the enclosed invention and process is to limit the potential errors associated with the traditional "copymill" process and create a more efficient process resulting in a less costly product that provides substantial time savings to both the dentist and the technician. The invented process will also provide a highly aesthetic and functional product that will meet the demands of both the dentist and the patient.

In the first embodiment of the invented process, the dentist and/or technician will create a stone cast 125 and diagnostic wax-up 130 as previously discussed. It is from these elements, where the invented process will allow for the simultaneous design and fabrication of the crowns and framework. First a digital scan of the stone cast 125 utilizing the alignment posts 156 attached to the analogs 124 as detailed in application Ser. No. 11/875,826, is conducted. This process will determine the exact location of the critical mating geometries and their correlation relative to one another as well as relative to the soft tissue contours captured in the stone cast. As demonstrated in FIG. 12, in step 214 of the process, the dentist sends the stone cast 125 and diagnostic wax up 130 to the laboratory. In step 216, the laboratory inserts alignment posts 156 into the analogs 124 embedded in the stone cast 125. These alignment posts 156 are configured to engage the mating surfaces of analogs 124 and hold the alignment posts coaxial with the longitudinal axis of analogs 124. They may have differently shaped flat, frusto-conical and cylindrical surfaces configured to engage with the mating surfaces of analogs 124. The alignment posts 156 used in this process have two spherical surfaces comprising centers coaxial with analog 124. These alignment posts need not have spherical surface portions, but may have any predetermined geometric shape as deemed suited by the user. This process also encloses the use of a single gauge; however it can be appreciated that a series of gauges could be used instead of a single embodiment to achieve the same result.

The mating surfaces on the alignment posts and the mating surfaces on the analogs 124 inter engage to cause the alignment posts 156 to be aligned coaxial with analogs 124. The alignment posts 156 cover the free ends of the analogs 124 exposed in stone cast 125.

In step 218, once the alignment posts 156 have been attached to the analogs 124, the scanner 182 is configured to scan the alignment posts and the soft tissue replica of the patient's mouth formed in the surface of the stone cast 125, and the alignment posts 156. The surfaces of stone cast 125 that are scanned by scanner 182 include the surfaces of the stone cast that replicate the mucosal tissue in the patient's mouth. Scanner 182 stores in the memory of computer 186 a first point cloud dataset of the stone cast 125 with alignment posts 156 attached. In step 218, scanner 182 also scans the surface of diagnostic wax-up 130 and the surface of stone cast 125 (preferably when they are assembled) and saves a second point cloud dataset collectively representing the scanned surface of the diagnostic wax-up 130 and stone cast 125. Alternatively, the operator can scan the diagnostic wax-up 130 separately from the stone cast and later register the point cloud dataset of the stone cast 125 and the diagnostic wax-up 130.

If the diagnostic wax up 130 is scanned on the stone cast 125, the scan preferably includes data points taken from all the exposed external surfaces of the diagnostic wax-up 130 (i.e. the outwardly facing surfaces that model the gum and the teeth) as well as surfaces of the stone cast 125 adjacent to the diagnostic wax-up 130. The surfaces of the stone cast 125 adjacent to the diagnostic wax-up that are scanned in the second point cloud dataset are also preferably scanned in the first point cloud dataset and thus there is some overlap in surface contours in both the first and the second point cloud datasets—both datasets include data points scanned from the same surfaces of stone cast 125. This permits later registration of the first and second point cloud datasets.

If the diagnostic wax-up 130 is scanned when it is separate from the stone cast 125, it is preferably scanned so that the second point cloud dataset includes data points taken from all the exposed external surfaces of the diagnostic wax-up 130 (i.e. the outwardly facing surfaces that model the gum and the teeth) as well as surfaces of the diagnostic wax-up 130 that would abut stone cast 125 if the diagnostic wax-up 130 was mounted on the stone cast. Since the diagnostic wax-up 130 was formed by molding a plastic (or wax or acrylic) material to the surface of the stone cast 125, the scanned surface contour of the diagnostic wax-up 130 that abut the stone cast are a mirror image of surface contours of the stone cast 125.

In the preferred embodiment these abutting stone cast 125 surfaces were scanned previously and are a part of the first point cloud dataset. Thus, the first and second point cloud datasets include a subset of data points taken from mirror image surface contours—surface contours common to both the first and second point cloud datasets—common to the diagnostic wax-up 130 and to the stone cast 125. This permits later registration of the first and second point cloud datasets.

In step 220, computer 186 determines the location and orientation of the alignment posts as they are attached to analogs 124 in the stone cast 125. Computer 186 sequentially selects a digital parameterized fitting 152" from its internal library and aligns the mating surface (or surfaces) and axis of the selected digital parameterized fitting 152" with the surface (or surfaces) and axis of one of the analogs based upon datums derived from the alignment posts 156. Computer 186 repeats this process for each additional analog 124 whose location and orientation were determined in step 220, until it has built up an initial surface model of dental framework 324.

In step 222, a surface model of the unique contours of stone cast 125 is created which is a representation of the soft tissue contours in the patient's mouth. The stone cast surface model 320 will provide a lower limit to which the framework can be designed to.

In step 224, a surface model of the unique contours of diagnostic wax up 130 is created which is a representation of the proposed prosthesis for the patient. The diagnostic wax-up surface model 322 contains the unique buccal/facial and occlusal contours of the denture teeth 132. The diagnostic wax-up surface model 322 will provide the necessary information regarding the orientation of the individual denture teeth 132 as they are positioned relative to one another within diagnostic wax-up 130.

The surface models 320 and 322 can be the raw point clouds derived from the scan data of the stone cast 125 and diagnostic wax-up 130 or can be a sheet body, where a surface has been wrapped across the raw point clouds.

The two sets of scan data and resulting surface models of the stone cast 125 and diagnostic wax-up 130 provide all of the necessary data for determining the position of the denture teeth 132 in diagnostic wax-up 130 relative to the implants and abutments and the soft tissue contours of stone cast 125 as well as defining the boundaries or limits in which the framework should be designed within. The scan data of the diagnostic wax up 130 will provide all of the necessary positional information for determining the correct orientation of the crowns and related support posts (For the remainder of the patent application, the inventor will be using the term prep tooth forms or PTF in place of the term support posts. Both prep tooth forms (PTF) and support posts are descriptive of the portion of the framework that will mate with and support the crown.).

Figure 13:
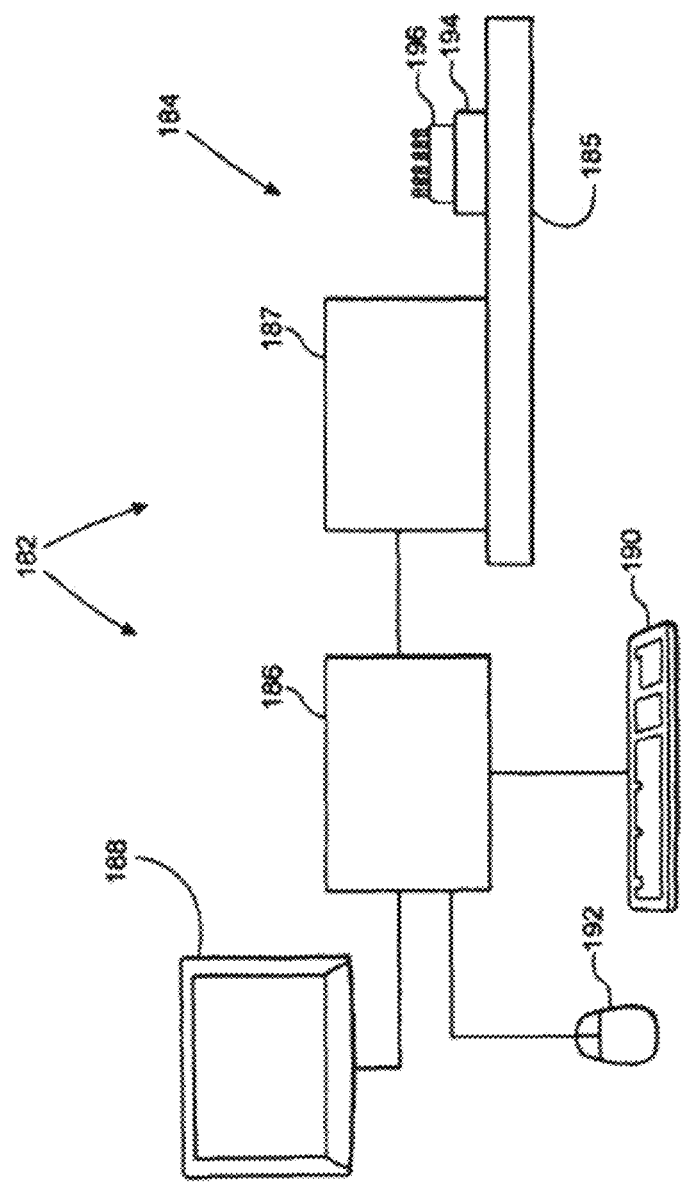
FIG. 13 is a schematic diagram of the scanner and the wax-up framework and alignment posts that it is scanning.
Figure 14A:
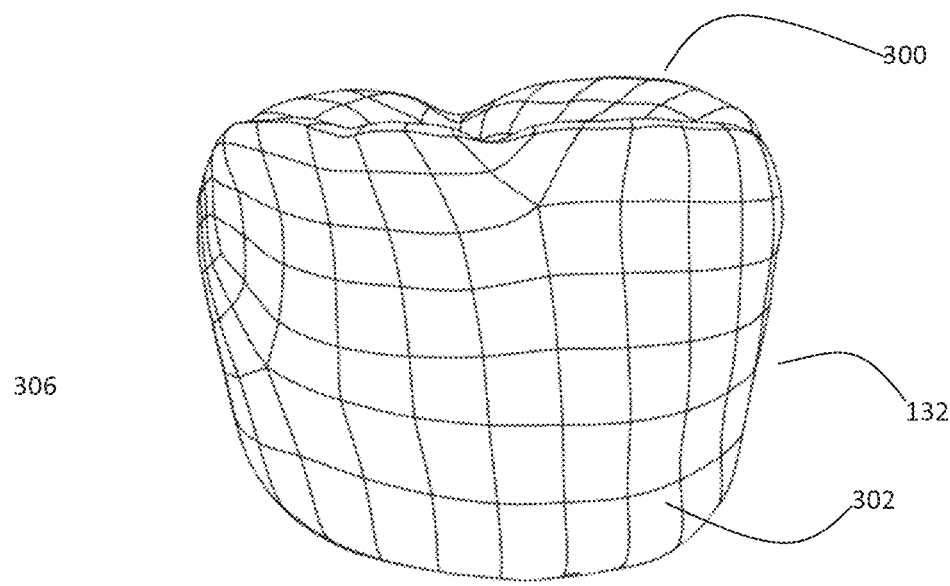
FIG. 14A is a front view of the graphical representation of the surface model scanned from the denture tooth.
Figure 14B:
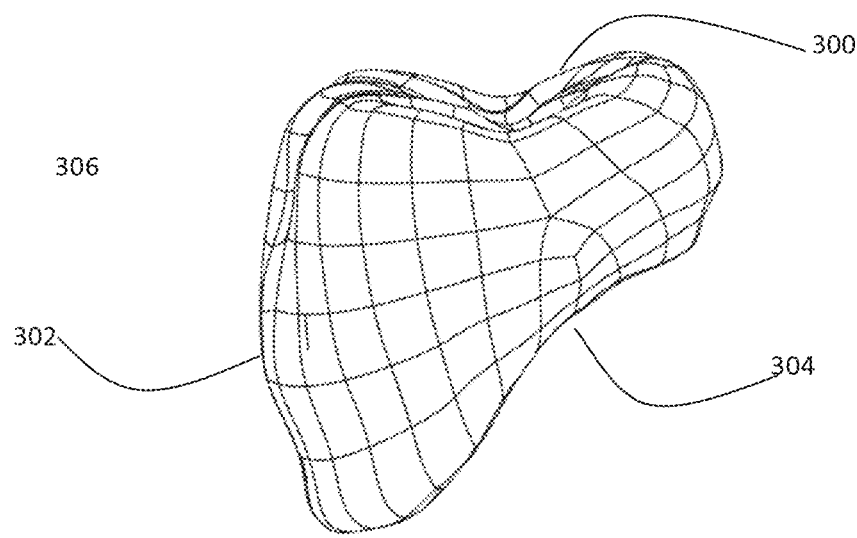
FIG. 14B is a side view of the graphical representation of the surface model scanned from the denture tooth.
Figure 15A:
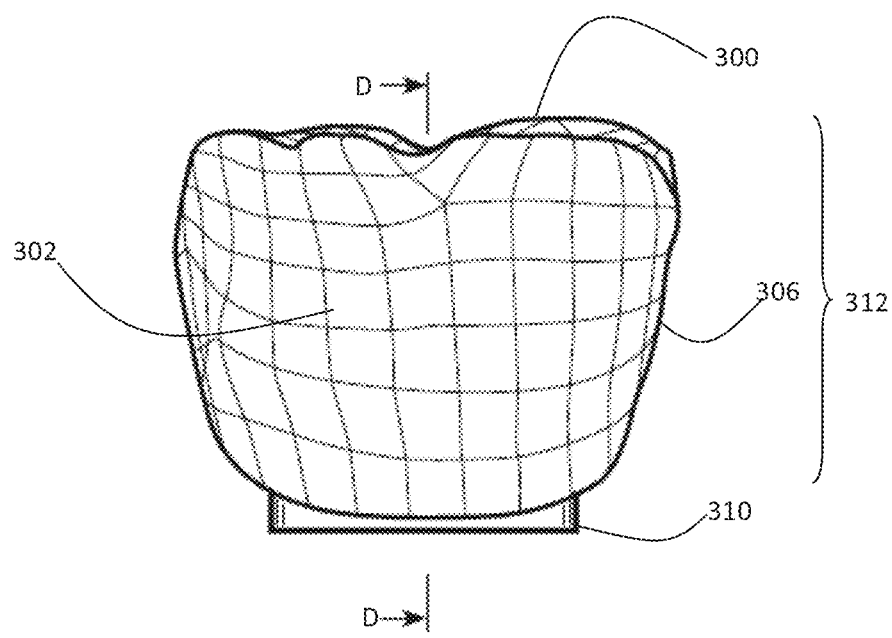
FIG. 15A is a front view of the graphical representation of the Crown and Support Post/Prep Tooth Form models.
Figure 15B:
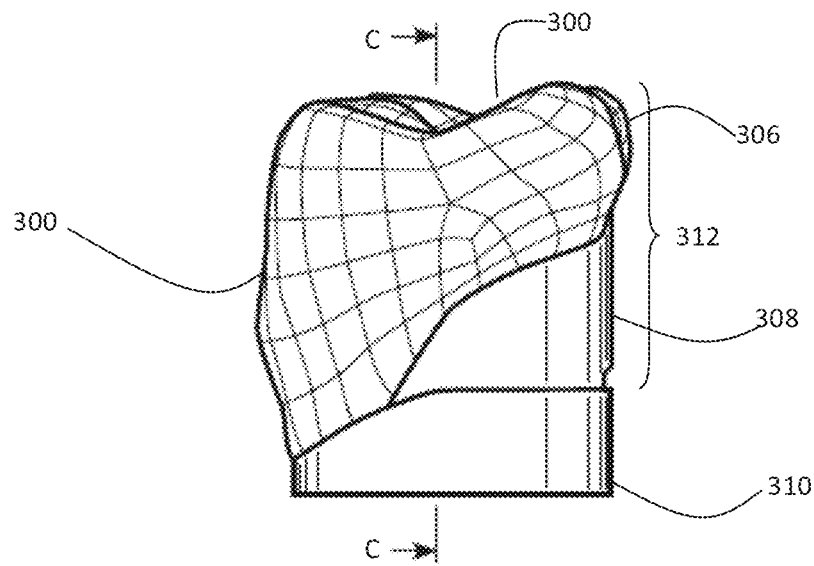
FIG. 15B is a side view of the graphical representation of the Crown and Support Post/Prep Tooth Form models.
Figure 15C:
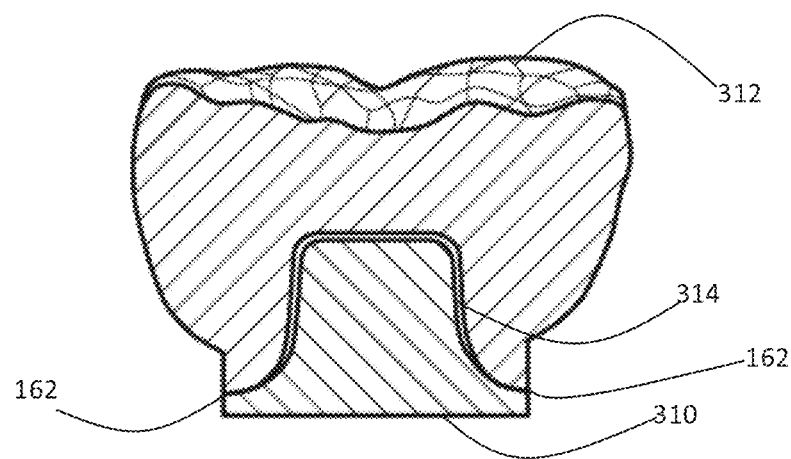
FIG. 15C is a cross sectional view of the Crown and Support Post/Prep Tooth Form models of FIG. 15B taken at section line C-C in FIG. 15A.
Figure 15D:
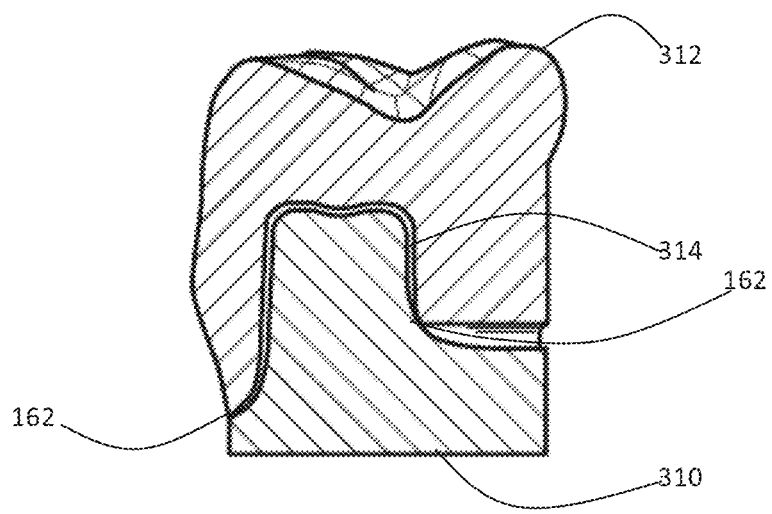
FIG. 15D is a cross sectional view of the Crown and Support Post/Prep Tooth Form models of FIG. 15A taken at section line D-D in FIG. 15B.

The invention is created through a novel concept in utilizing a library of crown models and prep tooth forms (support posts). The crown models are based upon known dimensions of standard tooth sizes. Many of the current dental design software systems, such as *Procera,* 3Shape, or Dental Wings, have a library of digital crown or tooth files based upon these standard dimensions. Stock Denture Teeth are also constructed on the basis of the standard tooth size and are commonly used in the construction of dentures, over-dentures, and fixed hybrid restorations for treatment of the edentulous patient. Also some of the previously mentioned software systems include models of the denture teeth in their library. For the first embodiment of the invention, the inventor will be focusing on the use of stock denture teeth. As discussed previously, these denture teeth 132 are commonly used in the dental market and consist of known dimensions that have been standardized for mass production. By utilizing a non-contact or touch probe scanner similar to the one described in FIG. 13, an operator can capture the unique contours of the commonly available denture teeth 132 that are used by the dentist or technician in creating the diagnostic wax up 130. FIGS. 14A-B show a model of the reverse engineered denture tooth and shows the unique occlusal contours 300 and buccal/facial contours 302 captured during the scanning process. The scanning process will also capture the intaglio surface 304 or underside of the denture tooth, which will enable for the creation of a denture tooth model 306. On the basis of the denture tooth model 306 and occlusal contours 300 and buccal contours 302, a PTF 310 can be designed to optimally support a crown that has the same or similar contours as the denture tooth. The Prep Tooth Form or PTF 310 can be designed to accommodate an appropriate wall thickness of the crown and provide an ideal margin 162 where the crown will mate with the framework. The crown model 312 consists mostly of the contours of the reverse engineered denture tooth 132 captured in denture tooth model 306, but additional features or material can be added to the crown model in generating an ideal mating surface that will interface with the PTF or provide an ease in manufacturing. The added lingual crown material 308 as shown in FIGS. 15A and 15B has been included into the design to create a more planar mating surface or margin 162 between the crown model 312 and PTF 310. However it can be appreciated that the mating surface or margin 162 can be non-planar and provide a margin 162 that is more in line with one that the dentist or technician would find for a prepped tooth or custom abutment. The lingual crown material 308 can be designed to aid during the gingival masking process. In this example, straight parallel walls have been included into the design to improve the retention of the crowns after acrylic processing. An appropriate cement gap 314 also has to be designed into the crown model 312 to provide the necessary space for dental cement that will allow for the crown to be fixated to the framework. The cement gap 314 will terminate at margin 162, where the crown and framework will ultimately mate.

The crown model 312 can be designed in a parametric or non-parametric CAD body. In the non-parametric form, the crown model is a rigid duplicate of the denture tooth model 306. This non-parametric model does not provide the CAD Operator with an ability to easily modify the surface or contours of the crown model 312. For a non-parametric CAD body, the operator will have to use Boolean and Trim functions to add or subtract additional features in order to change the occlusal contours 300 and buccal contours 302 of the crown model 312. In comparison the parametric CAD body can be constructed of a series of splines and sheets, possessing data points or poles, allowing for the CAD Operator to modify or alter the surface of the crown model 312.

The parametric CAD body allows for easy manipulation of the crown model surface to accommodate any design requirements required by the dentist. One example of manipulating the crown model surface would be modifying the occlusal contours of the crown. The dentist or technician may choose to lower or heighten all or portions of the occlusal surface to provide an ideal occlusal relationship with the opposing arch. Another example would be modifying the mesial/distal side contours in order to increase or decrease the mesial/distal contacts between the crowns.

FIGS. 15A-F depict an exemplary crown model and PTF. FIGS. 15A-F depict a molar crown model 312 and PTF 310. For demonstration purposes this application will only show the design of a crown model and PTF for a molar tooth. It can be appreciated that the PTF can be designed to properly accommodate any size tooth, such as an incisor, cuspid, or premolar. It can also be appreciated that any denture tooth system can be incorporated though the disclosed process. There are also available libraries of stock crown CAD files, in many of the dental design systems that can be incorporated and utilized in addition to reverse engineering the stock denture teeth. The PTF 310 has been designed to properly support the cusp structure of the reverse engineered denture tooth and the designed crown model 312. The design of the PTF 310 can also be modified in any way deemed appropriate by the designer to meet the requests of the customer. The height and width of the PTF can be altered to better deal with the restorative space presented with the case. The enclosed PTF design has a much more flat and planar design associated with the margin 162. Other designs may utilize a much more natural root form margin that comes up higher in the mesial/distal aspects of the crown and lower in both the lingual/buccal aspects.

Figure 15E:
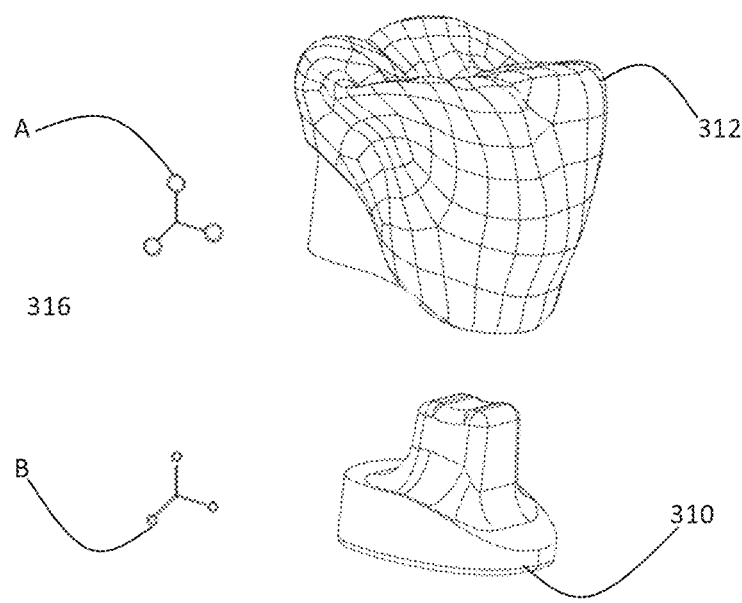
FIG. 15E is a perspective view of the Crown and Support Post/Prep Tooth Form models demonstrating their alignment separate from one another possessing independent coordinate systems.
Figure 15F:
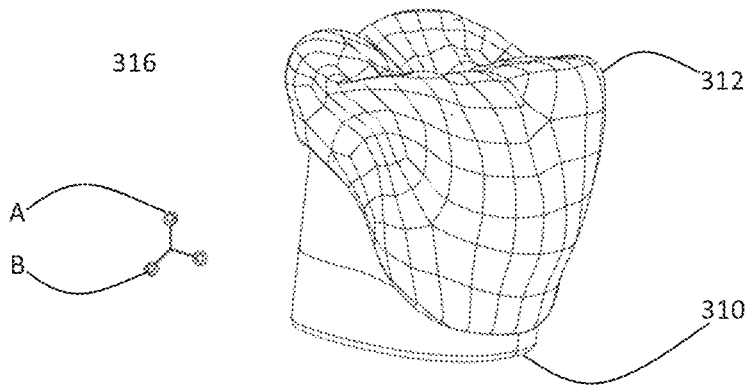
FIG. 15F is a perspective view of the Crown and Support Post/Prep Tooth Form models aligned correctly relative to one another and showing their individual coordinate systems aligned correctly to one another.
Figure 15G:
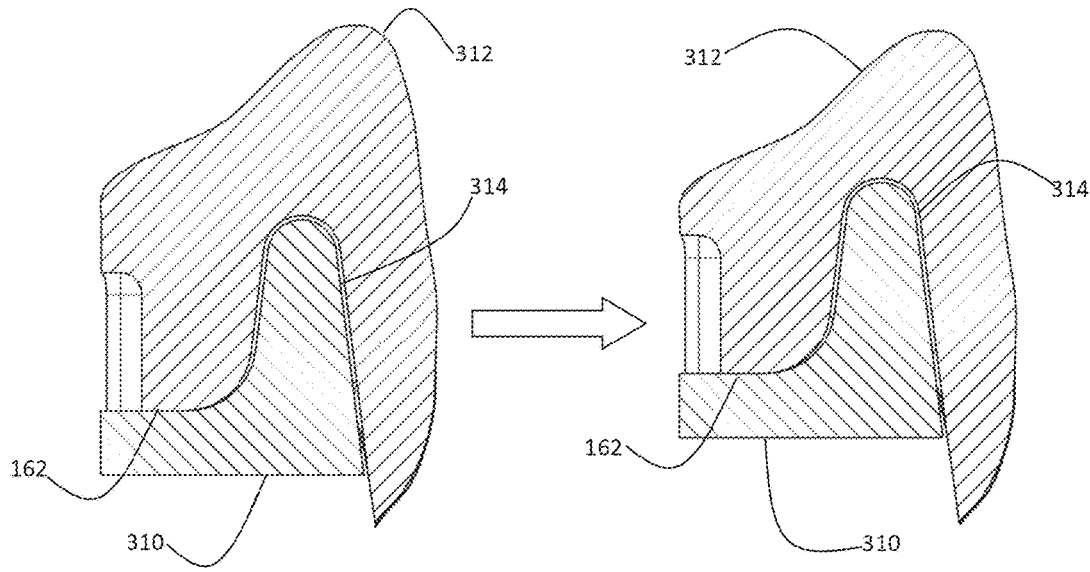
FIG. 15G is a cross-sectional view of a Crown and Support Post/Prep Tooth Form Model and demonstrates the feature dependency created between the Crown and Support Post/Prep Tooth Form models, where the cement gap and margin have been automatically updated based upon the Support Post/Prep Tooth Form being positioned higher.
Figure 15H:
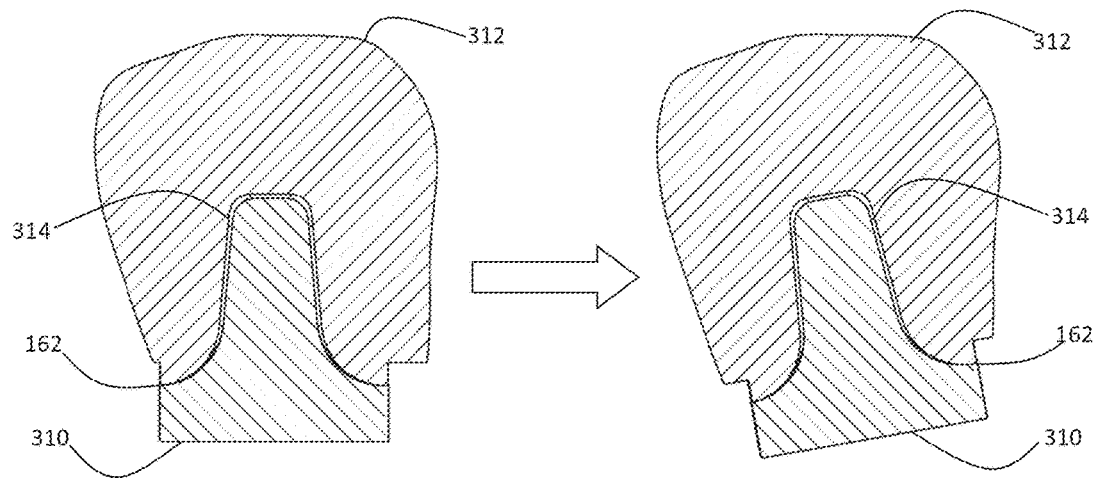
FIG. 15H is a cross-sectional view of a Crown and Support Post/Prep Tooth Form Model and demonstrates the feature dependency created between the Crown and Support Post/Prep Tooth Form models, where the cement gap and margin have been automatically updated based upon the Support Post/Prep Tooth Form being angulated to a new orientation.

As demonstrated in FIGS. 15E-F the crown model and PTF can be combined into assembly 316 and share the exact coordinate system, allowing for them to be aligned relative to one another in an ideal fashion. Assembly 316 allows for the crown model 312 and PTF 310 to be readily imported and remain properly aligned relative to one another. However it can also be appreciated that the crown model 312 and PTF 310 can be imported separately depending upon the CAD system or processes being implemented by the Operator. One example of importing PTF's 310 without the crown files would be if the dentist or technician is planning on creating custom crowns for the final restoration. In this instance the utilization of the crown files may be completely unnecessary and the operator can position PTF 310 in the ideal position to support the crown. This exemplary process would also allow the technician to utilize one of the other dental design software packages previously mentioned to design and fabricate the crowns, in a similar fashion as through the "copymill" process.

FIGS. 15 A-D show in closer detail crown model 312 aligned appropriately to PTF 310. As depicted in the figures the PTF 310 expands substantially to support the crown model 312 in the mesial distal aspect FIG. 15 A and the lingual facial aspect FIG. 15 B. FIGS. 15 C and D are cross-sectional views of the crown model 312 and PTF 310 showing the cement gap 314 and margin 162 where the crown intimately mates with the PTF. The cement gap 314 and margin 162 can be adjusted by the designer to meet the customer requirements or to better suit the preferred manufacturing process. FIGS. 15 A-F show the ideal orientation of the crown model and PTF. However there are instances when this orientation may not be ideal due a design requirement for a particular case. The crown model and PTF can have a series of dependent features that when a change in the feature of one body is performed, the second dependent body will automatically update based upon this change. One example would be repositioning the height of the PTF. As demonstrated in FIG. 15 G, when the PTF is positioned higher relative to the crown model 312, the cement gap 314 and margin 162 will automatically update to accommodate for this new position. The crown model 312 and PTF 310 can also be allowed to be positioned in different orientations relative to one another and similarly update on these new positions. Another example as demonstrated in FIG. 15 H would be repositioning the angle of the PTF due to an issue of path of insertion or tool access for manufacturing. As shown in FIG. 15 H, when the PTF is aligned to the new position not only does the cement gap 314 update, but also margin 162 will update to this new alignment. This dependency provides the ability for the designer to make simple modifications in a timely fashion when designing the framework in accommodating a design request for a customer or allowing for an ease in manufacturing.

The Crown/PTF Assembly 316 can possess additional sub features in addition to the full contour crown surface. The crown model can have subtract features which will provide the technician and dentist with a standard coping or cutback coping that would be ideal in stacking porcelain. The standard coping or cutback coping can be included through the use of a Boolean Subtract Feature or as a separate CAD body within the Crown/PTF Assembly 316. The inclusion of these features provides a broad spectrum of restorative elements for the dentist or technician to choose from.

Figure 12:
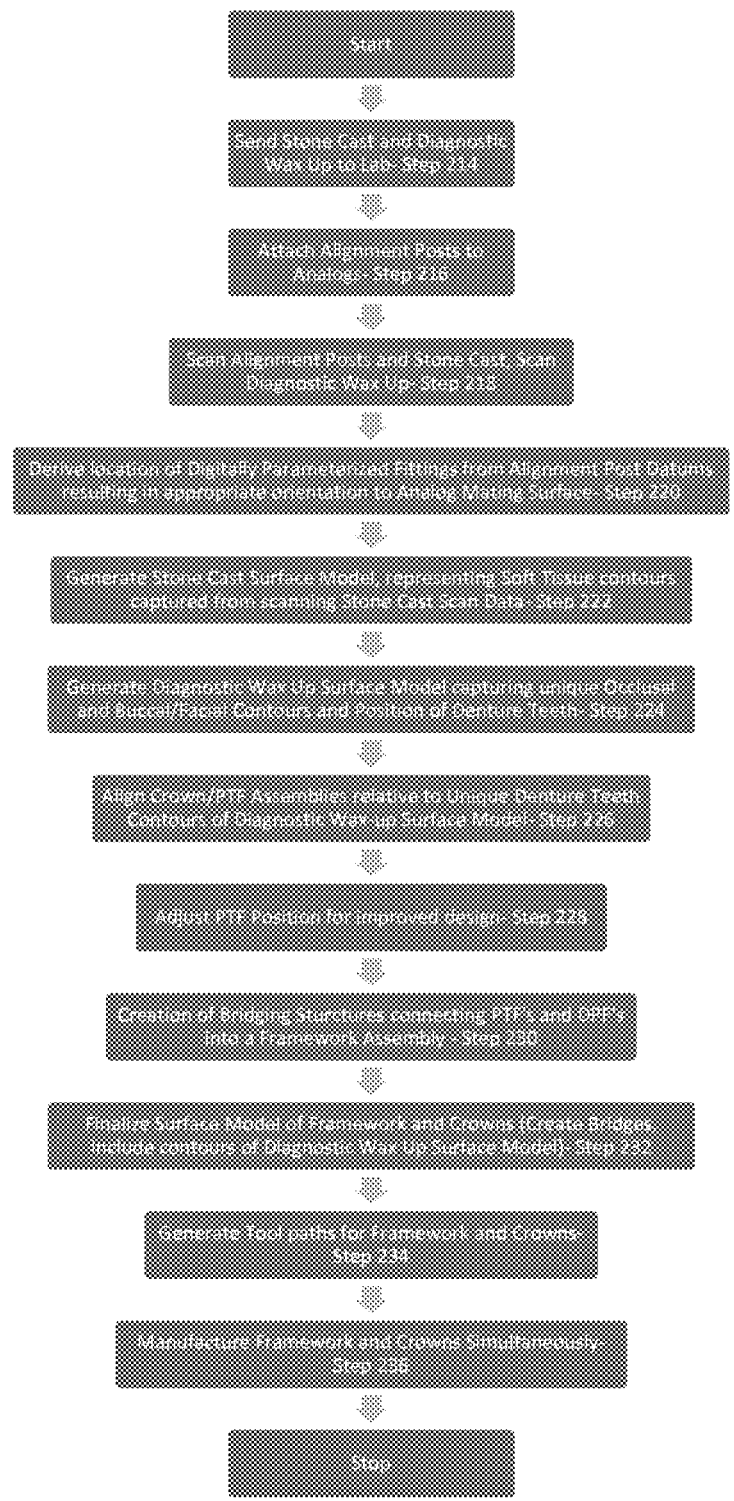
FIG. 12 is a flow chart demonstrating the steps for the new invented process and invention.
Figure 16A:
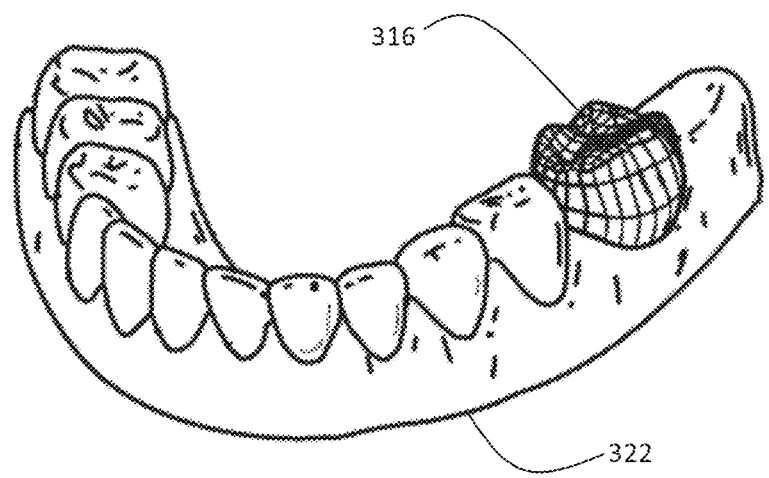
FIG. 16A is a graphical representation of diagnostic wax up surface model with one of the Crown and Support Post/Prep Tooth Form assemblies appropriately aligned.
Figure 16B:
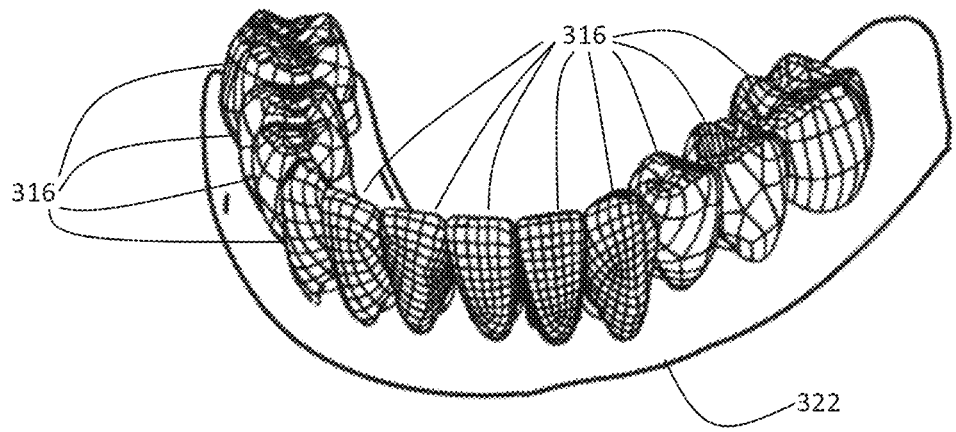
FIG. 16B is a graphical representation of diagnostic wax up surface model with all of the Crown and Support Post/Prep Tooth Form assemblies appropriately aligned.

In step 226 of FIG. 12, the Crown/PTF Assembly 316 is imported and aligned relative to the diagnostic wax-up surface model 322. The crown/PTF assembly 316 will have the same surface contours as one of the denture teeth 132 that was incorporated into diagnostic wax up 130. Utilizing a best fit operation, the crown/PTF assembly 316 will be properly positioned on the basis of the facial/buccal and occlusal contours for the specific denture tooth 132. FIGS. 16 A-B demonstrate this process. In FIG. 16A, a molar crown/PTF assembly 316 is aligned appropriately to diagnostic wax-up surface model 322. In FIG. 16B, the additional crown/PTF assemblies are aligned for the incisors, cuspids, premolars, and remaining molar. This alignment process can be carried out by computer 186 automatically or overseen and performed manually by the operator.

Figure 17:
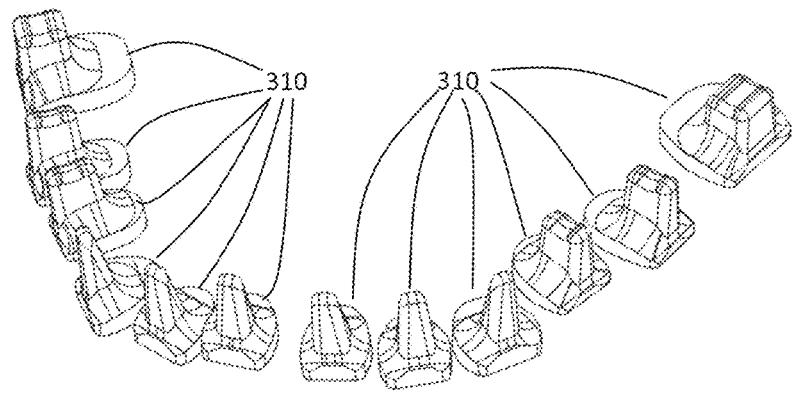
FIG. 17 is a graphical representation of the Support Posts/Prep Tooth Forms in their appropriate alignment based upon the diagnostic was up surface model.
Figure 18:
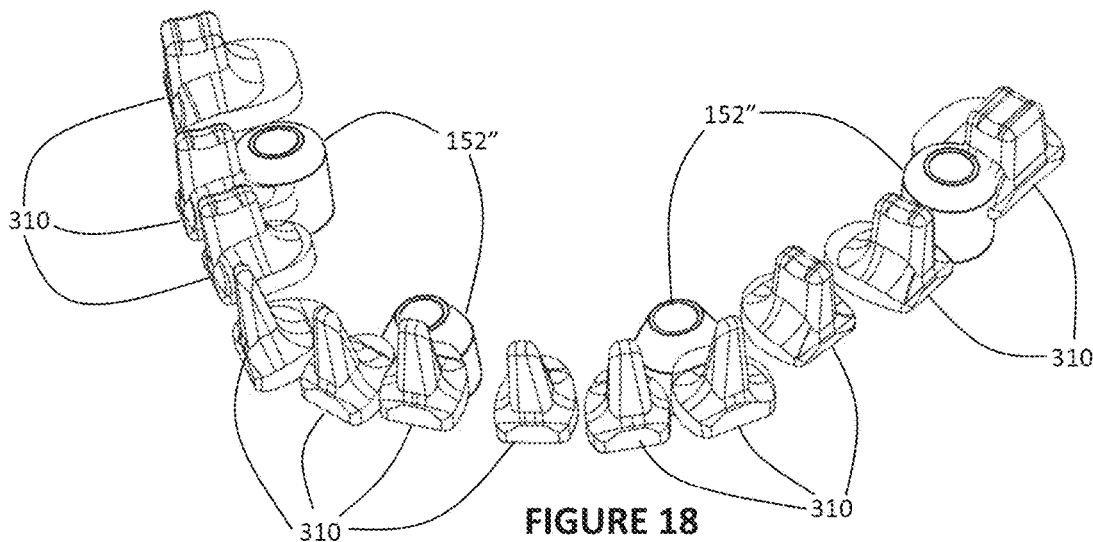
FIG. 18 is a graphical representation of the DPF's and Support Posts/Prep Tooth Forms appropriately positioned relative to one another in creating the surface model of the framework.
Figure 19A:
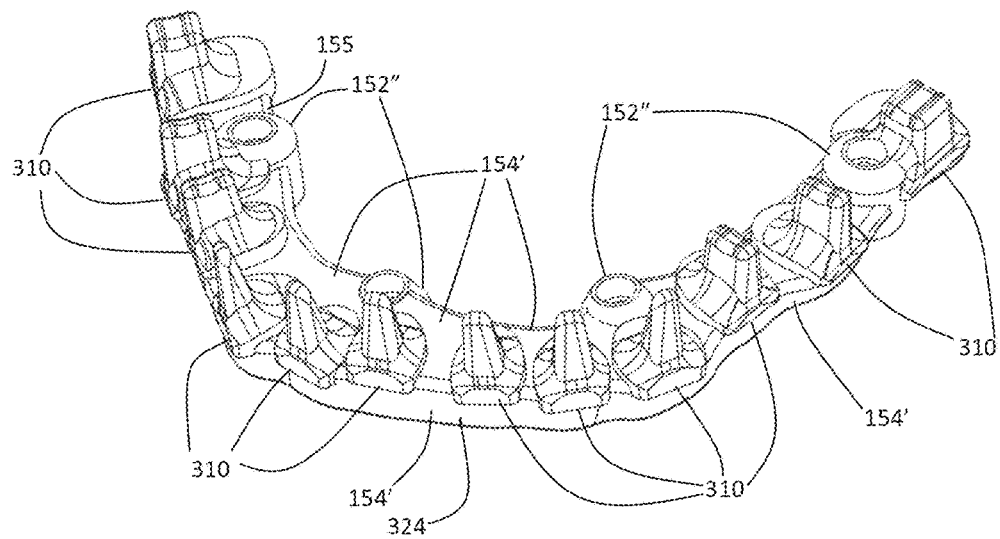
FIG. 19A is a perspective view of the surface model of the framework with the DPF's, Support Posts/Prep Tooth Forms, and Bridging Structures appropriately positioned relative to one another.
Figure 19B:
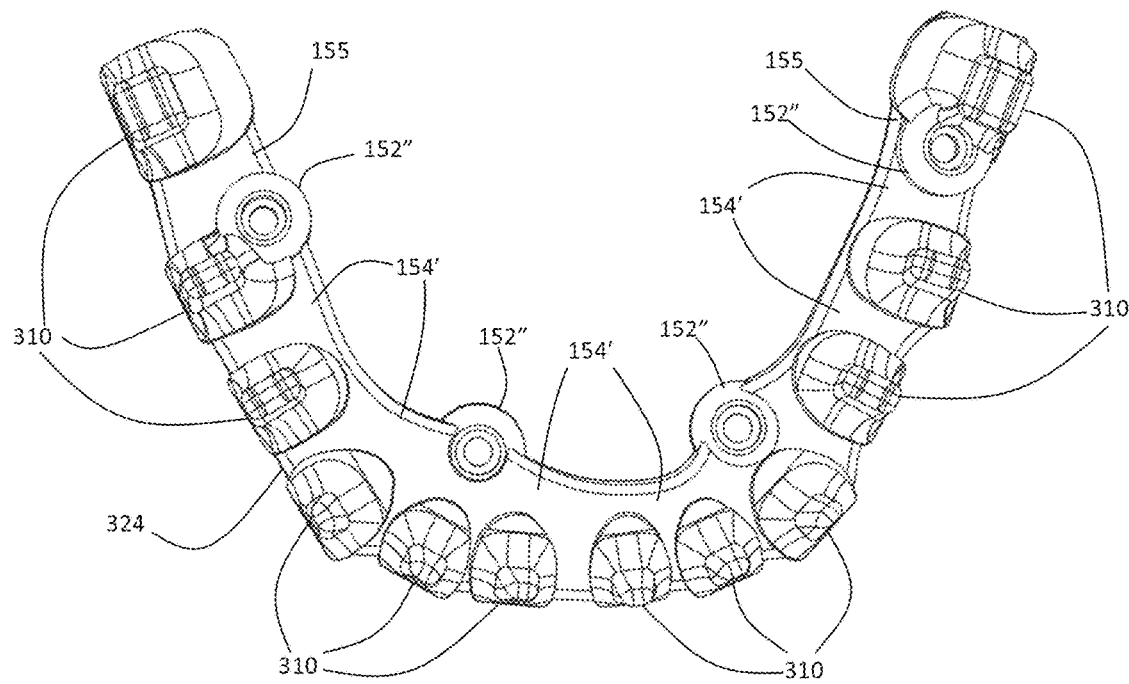
FIG. 19B is a top view of the surface model of the framework with the DPF's, Support Posts/Prep Tooth Forms, and Bridging Structures appropriately positioned relative to one another.

In Step 228, the Operator will review and adjust the position of the PTF's 310 to best accommodate the aesthetic and functional demands for the case. As discussed above, this process of moving the PTF's 310 can also accommodate for improved tool access on the basis of the manufacturing method. Once appropriately positioned into the proper orientation, the cement gap 314 and margin 162 will automatically update on the basis of this new position. FIG. 17 shows all of the PTF's 310 in there appropriate position, while the crown models 312 and diagnostic wax-up surface model 322 are hidden. FIG. 18 shows the PTF's 310 and DPF's 152" properly positioned relative to one another. In step 230, the computer 186 is configured to generate a surface model of bridging structure 154' (FIGS. 19 A-B) that will join PTF's 310 and the digital parameterized fittings 152". This includes the computer 186 determining the cross-sectional shape, length and location of the bridging structures as described below. This surface model of this bridging structure 154' extends between and joins PTF's 310 and the digital parameterized fittings 152" and thereby completes the surface model of the dental framework 324. Bridging structure 154' also comprises the portions 155 that extend away from the end digital parameterized fittings 152" and are supported only at one end. One form of the bridging structure is shown in FIGS. 19A-B as a simple elongated member having a predetermined cross section.

To generate bridging structure 154', computer 186 determines the shape, length, and location of the individual portions of the bridging structure to attach PTF's 310 and digital parameterized fittings 152". It is further configured to determine the shape length and location such that the individual portions will not intersect the stone cast surface model 320. Since the surface of the stone cast 125 represents the exposed surfaces (including mucosal tissue) in the patient's mouth, this reduces the likelihood that the physical framework created from the surface model will contact and damage the patient's mucosal tissue. Computer 186 is configured to provide a separation distance between the surface model of the stone cast and the bridging structures. In one arrangement the computer 186 is configured to place the bridging structures a predetermined minimum distance from the surface model of the stone cast. In another arrangement the computer is configured to permit the operator to select a desired minimum distance between the bridging structure and the stone cast surface model 320. In another arrangement, the computer is configured to offer to and/or accept from the operator only a certain range or number of minimum separation distances, such minimum separation distances preferably ranging between 0.1 mm and 5 mm.

Computer 186 is configured to create the bridging structure by providing a pre-designed list of bridging structure forms (e.g., a cylinder, circle, ellipse, square, polygon or other geometric shape) that have been previously stored in the electronic memory of the computer. In one configuration, the computer is configured to automatically select the cross sectional dimensions of each form (diameter, radius, major and minor diameter, height, width, etc.). In another configuration the computer is configured to present the user with a list of pre-set values or defined by the user among which the user can select preferred dimensions. In yet another configuration, the computer is configured to prompt the user to enter specific numeric values for these dimensions. The form of the bridging structures can also be defined by the user.

Computer 186 is configured to determine the proper location of the bridging structure 154' extending between the PTF's 310 and the digital parameterized fittings 152" by locating the beginning and end of each structure according to position information that is derived from the scanned point cloud dataset of the alignment posts. Position of the bridging structure can also be determined by the operator or from the point cloud data set of the stone cast and/or diagnostic wax up.

In another arrangement, the computer 186 is configured to determine the location of the bridging structure 154' extending from each of the PTF's 310 and digital parameterized fittings 152" by locating the beginning and end of each structure according to reference points and axes assigned to the digital parameterized fittings 152" by the computer program from a list of pre-set values or defined by the user. For example, each PTF 310 and digital parameterized fitting 152" which is placed in the model may have only certain types of bridging structures to which they can be connected, and may only connect to those bridging structures at certain locations on the PTF or digital parameterized fitting. This information is stored in the electronic memory of computer 186 in association with each PTF or digital parameterized fitting. When a particular PTF or fitting is inserted into the model, computer 186 is configured to the type and location information associated with the inserted PTF or fitting and locate (or permit the operator to locate) bridging structures of the type and at the locations compatible with those PTF's or fittings. This process can also ensure the bridging structure does not extend into critical mating areas of PTF 310 and digitally parameterized fitting 152" that would affect the potential fit of the crowns or implant/abutments to the framework. In the case of distal extensions 155, computer 186 is configured to cantilever them off the digital parameterized fittings 152" and extend them distally along the arch of the patient's mouth. These distal extensions 155 are preferably 20 mm in overall length or less. They are also selected as described above.

Computer 186 is configured to conduct a mechanical design analysis of the distal extensions 155 that validates shear and bending strength limits for those geometries relative to their chosen material and shapes. Computer 186 is configured to apply the appropriate shear, tensile and compressive stress analysis techniques to the chosen geometries automatically or from a pre-determined list of tests chosen by the user. Upon successful analysis of the distal extension designs, the extensions are verified or accepted by the user.

As part of the step of generating the bridging structure 154' computer 186 is configured to determine a location for the bridging structure 154' that will not intersect the diagnostic wax-up surface model 322. This ensures that the bridging structure 154' of the final denture framework will not stick through, but will be disposed within, the body of the diagnostic wax-up 130.

It can be appreciated that all of the disclosed steps being performed by Computer 186 can be performed manually by the Operator. The Operator can also determine the use of any number of custom geometries or series of geometries to be used for the bridging structure 154' and distal extensions 155.

Upon completion of the bridging structures 154' and distal extensions 155, the final surface model of the framework 324 is complete. The final surface model of the framework will consist of PTF's 310, DPF's 152", bridging structures 154' and distal extensions 155. FIGS. 19 A-B show the final surface model of the framework 324. Computer 186 will also determine any interference between the crown models 312 and the surface model of the framework 324 that may have been generated during the design process.

Figure 20A:
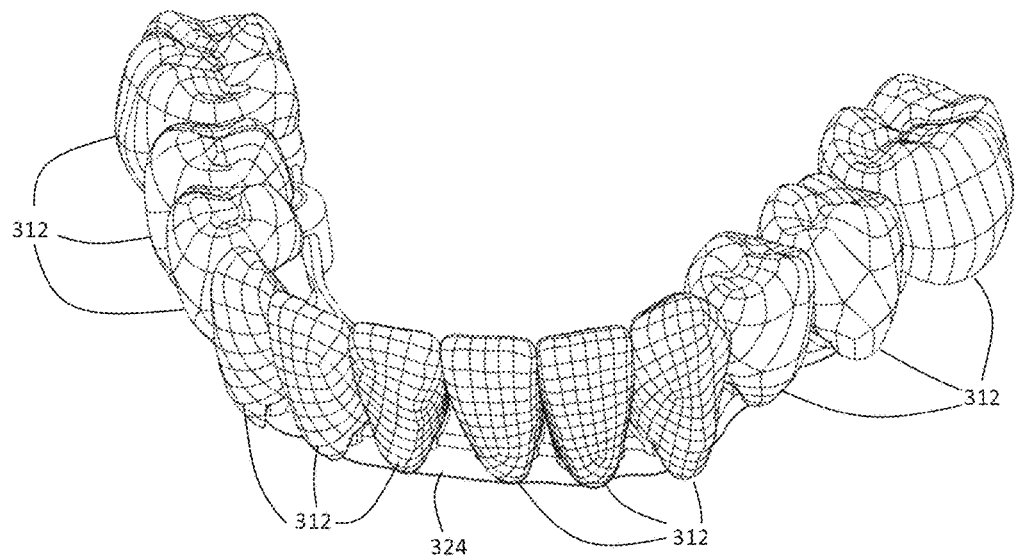
FIG. 20A is a perspective view of the surface model of the framework including DPF's, Support Posts/Prep Tooth Forms, and Bridging Structures with the crown models appropriately positioned.
Figure 20B:
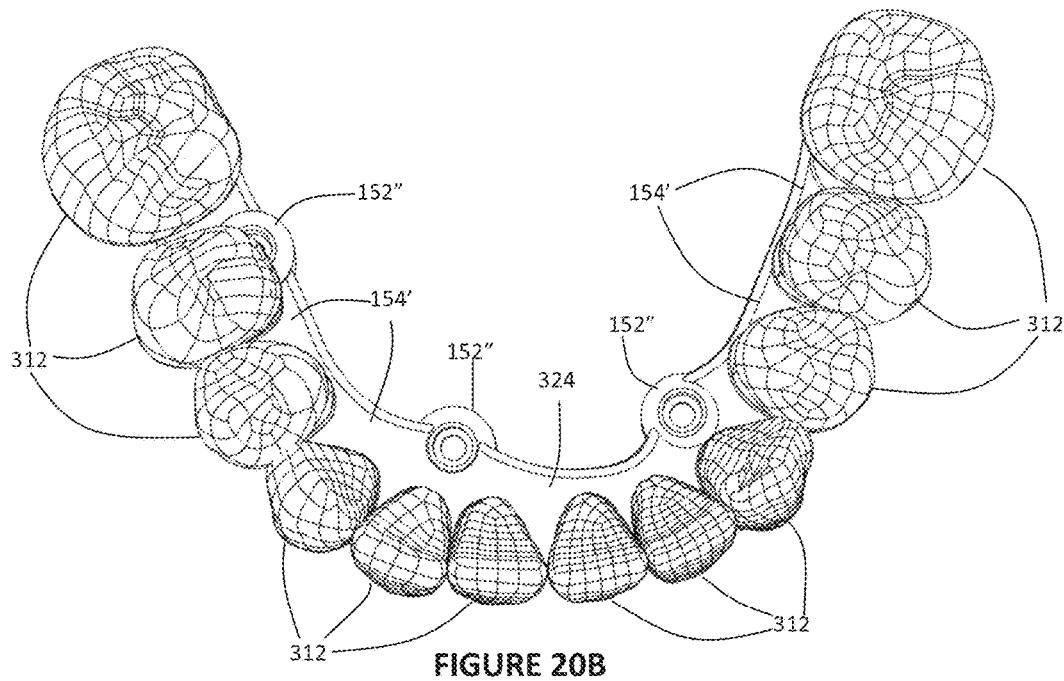
FIG. 20B is a top view of the surface model of the framework including DPF's, Support Posts/Prep Tooth Forms, and Bridging Structures with the Crown models appropriately positioned.

In STEP 232, Computer 186 will finalize the surface model of the framework and crowns by alleviating any interference between these surface models. This process is performed through a Boolean subtraction of the surface model of the framework 324 from crown models 312. FIGS. 20A-B show the crown models 312 and surface model of the framework 324 appropriately positioned relative to one another. At this time the Operator can also choose to include screw access holes into the crown models 312 at the request of the dentist or technician.

Figure 21:
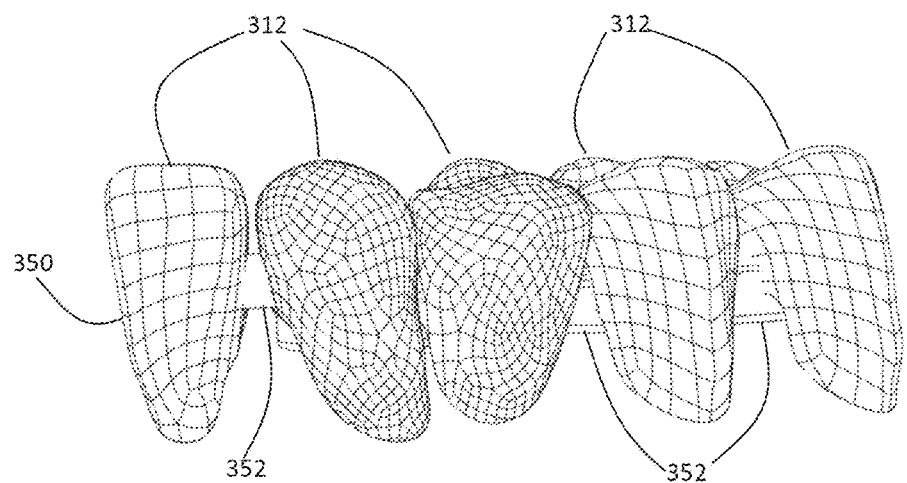
FIG. 21 is a side view of the Bridge model.

There also may be times when the dentist or technician may prefer the crown models 312 be adjoined to one another into a bridge due to design limitations associated with the case or to meet a personal preference of the dentist. In FIG. 21, crown models 312 have been adjoined to one another in creating bridge model 350. Through a Boolean Union or the addition of other CAD features herein referred to as bridge bodies 352, the crowns 312 can be adjoined to one another as best determined by the Operator and can include all of the crowns or as few as two. In FIG. 21 five crown models have been combined into forming bridge model 350 by means of bridge bodies 352. Bridge bodies 352 can consist of a standardized profile (e.g., a cylinder, circle, ellipse, square, polygon or other geometric shape) or the Operator can custom design an appropriate structure to provide the appropriate mechanical strength to resist against the occlusal forces of the patient's bite. If necessary the Operator can add appropriate features or geometries to ensure the bridging structure will properly mate to the framework and function under the occlusal loads of the patient. At times the creation of bridges or adjoining the crowns may be necessary due to the position of a screw access hole that would significantly reduce the size of a PTF 310 to a point where it would not be able to properly support a crown by itself. In this instance bridging the crown in this area to one or both adjacent crowns would prevent it from becoming damaged or dislodged when placed under occlusal loads by the patient.

Figure 22:
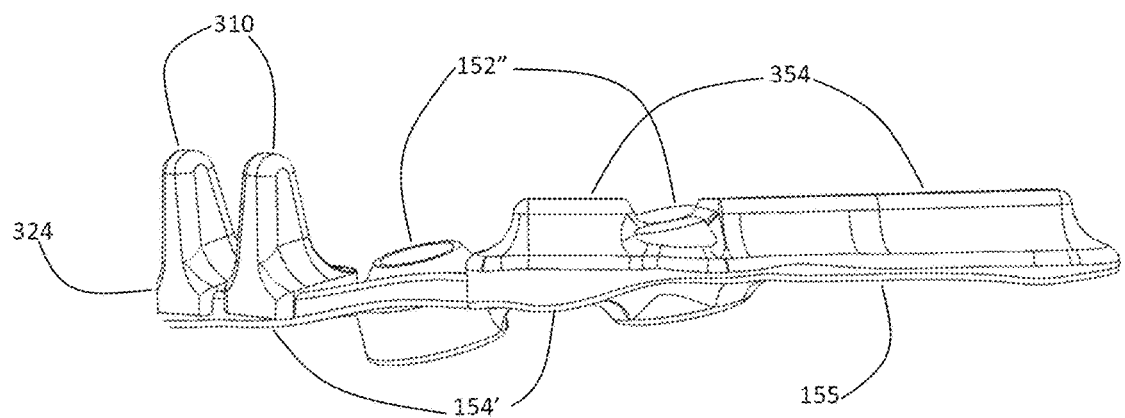
FIG. 22 is a side view of the framework model with a PTF Bridging Structure.
Figure 23A:
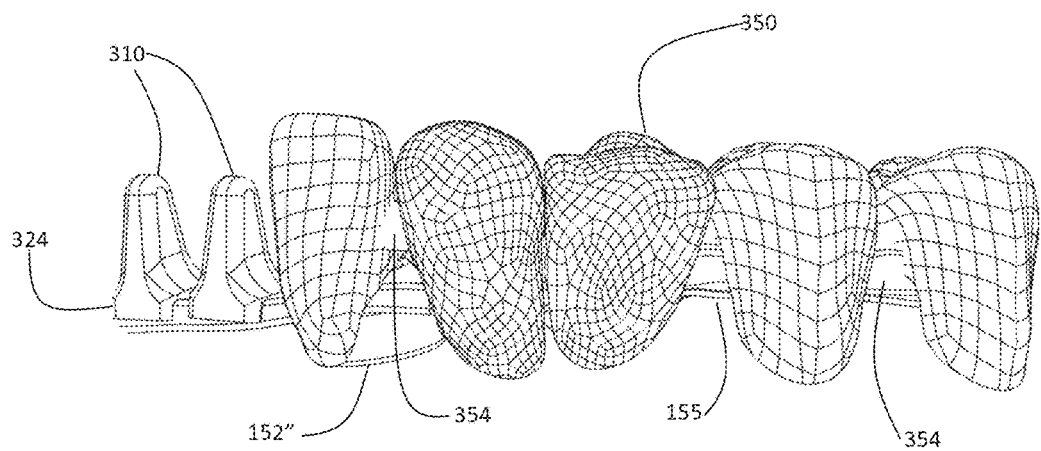
FIG. 23A is a side view of the framework model with the associated bridge model appropriately aligned together.
Figure 23B:
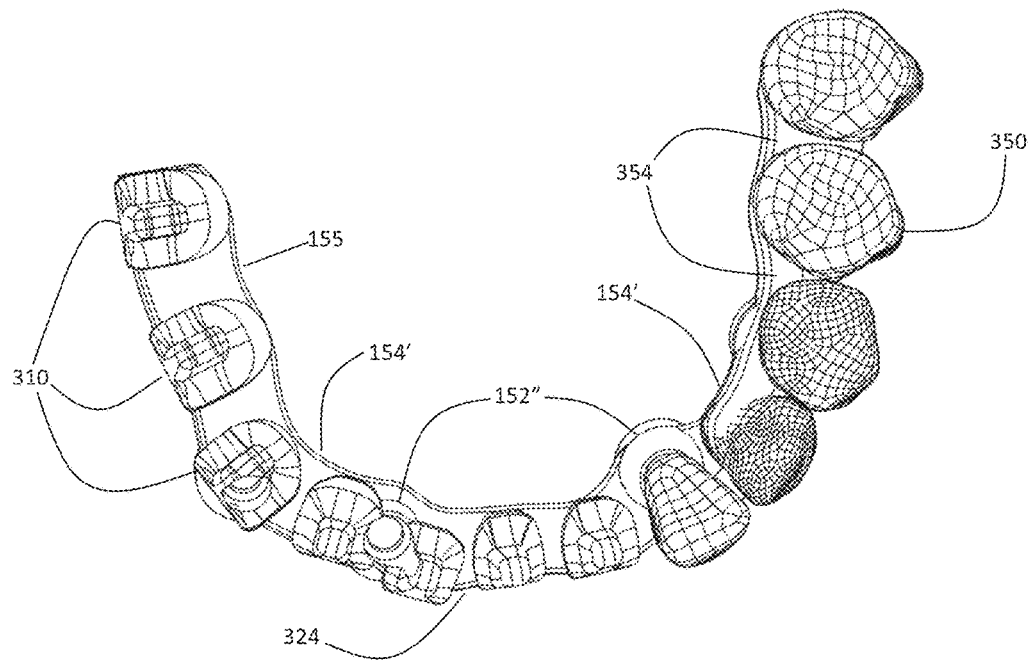
FIG. 23B is a top view of the framework model with the associated bridge model appropriately aligned together.

The operator may also determine it be best for the PTF's 310 be linked to one another in creating a larger support post geometry to support the overlying bridge. In the same manner that the bridging structures 154' are extended between the PTF's 310 and digitally parameterized fittings 152", a PTF Bridging Structure can be incorporated into the design either automatically by computer 186 or manually by the operator. This PTF Bridging Structure can consist of a standardized profile (e.g., a cylinder, circle, ellipse, square, polygon or other geometric shape) or the Operator can custom design an appropriate structure based upon the patients clinical conditions. The PTF Bridging Structure can have a constant cross-section or allow for portions of the PTF Bridging Structure to taper in from the buccal/lingual aspects to provide additional anti-rotation features when the overlying crowns or bridges are positioned on them appropriately. FIG. 22 shows a portion of framework model 324 with a PTF Bridging Structure 354 that has been created to support bridge 350. The PTF Bridging Structure extends across digitally parameterized fitting 152" in order to provide the necessary support for bridge 350. Due to the position of digitally parameterized fittings 152" and the resulting screw access holes, the standard PTF's were reduced drastically requiring for the creation of bridge 350 and the PTF bridging structure 354. FIG. 23 A-B show framework model 324 with bridge 350 properly positioned to one another.

It is also at this time that the Operator can choose to combine portions or the majority of the diagnostic wax-up surface model 322 to the crowns and/or bridge, to ensure the gingiva contours are included in the design. This process may be advantageous where there is limited space associated with the patient. In having the gingiva contours incorporated into the design, the operator can ensure the gingiva will have substantial strength characteristics as it is joined and fabricated from the same material as the crown or bridge. In the case of a full Zirconia restoration, the technician can apply coloring through stains and dyes in order to create the aesthetics for both the gingiva and crown portions. In addition to combining portions of the diagnostic wax up to the crowns in creating the gingival structures, the operator can choose to design custom gingiva features onto the crown utilizing the tools in the design software. This process would allow the operator to modify the contours to best meet the clinical demands of the case or to provide the best foundation for the finishing processes to be performed after the crown/bridge with gingiva has been fabricated. One example would be in the creation of gingival contours that would be ideal for porcelain stacking. Rather than having the exact contours of the diagnostic wax-up surface model 322, the preferred geometry may be the creation of a small shelf with the buccal aspect of the gingiva contour reduced slightly to accommodate the added thickness of the porcelain. The Operator could determine the appropriate dimension for the necessary porcelain, for example 1-2 mm, and create the appropriate trim or Boolean subtraction to reduce the gingiva contour from the diagnostic wax-up surface model 322 or custom design the appropriate gingiva construct manually using the CAD tools provided in the software.

In STEP 234, tool paths are generated for the surface model of the framework 324, crown models 312 and/or bridges 350. Since the orientation and position of the framework and crowns has been determined along with the orientation and position of the DPF's 152" and margins 162 (where the crowns mate to the framework), both the framework and crowns can be manufactured simultaneously in the chosen material (titanium, zirconia, wax, plastic, composites, acrylic, etc. . . . ) and through the preferred manufacturing process (milling, laser sintering, 3D printing, EDM, etc. . . . ).

Once the framework and crowns have been manufactured, they are delivered to the dentist and/or technician for the creation of the gingiva contours. The gingiva contours can be created by applying acrylic, composites, porcelain, or any other preferable dental material to the framework. If the gingiva contours were included in the design of the crowns, the technician will perform the necessary processing (i.e. staining, coloring, stacking porcelain . . . ) to complete the gingiva aesthetics.

The above disclosed invented process utilizes a traditional diagnostic wax-up 130, which provided the position of denture teeth 132 and ultimately PTF's 310 and crown models 312. In the first alternate embodiment of the invented process, the use of a virtual set up is used in place of the diagnostic wax-up 130. There are currently multiple dental systems and software (such as 3Shape, Dental Wings, Avadent and Procera) which have the ability to lay in CAD models of denture teeth or stock teeth relative to scans of a stone cast and an opposing dentition. For this first alternate process, the stone cast and opposing cast would be scanned separately and then scanned in their proper orientation relative to one another. Utilizing the scan capturing the orientation of the stone cast and opposing cast, the scan data of the stone cast and opposing cast will be properly aligned to one another. Once properly aligned, the Operator will position the CAD models of the denture teeth or stock teeth relative to the occlusion of the opposing cast. Once the position of the CAD models of the denture teeth or stock teeth have been finalized, this information can be used in aligning the crown and PTF assemblies 316 and begin designing the crowns and framework. In addition to utilizing the CAD models of the denture teeth or stock teeth, the operator can immediately begin utilizing the library of crown and PTF assemblies 316 and align the assemblies relative to the opposing cast for the proper orientation. This process may be advantageous over the previous described process as it alleviates the dentist and/or technician from having to create the diagnostic wax up. Also if the crown models are truly parametric, the operator can modify the design of the occlusal contours and buccal contours of the desired crown to meet any unique design requirements for the dentist.

In the second alternate process, the scanning process for capturing the implant and abutment positions is altered by the use of an intra-oral scanner that would directly capture the implant and/or abutment locations in the patient's mouth along with the gingiva contours. The intra-oral scanner can also capture the contours of a diagnostic wax up that has been placed in the patient's mouth or the position and orientation of the opposing arch during the scanning process. From this digital data, the dentist or technician can identify the appropriate location of the Crown/PTF Assemblies 316 and digitally parameterized fittings 152". This process would alleviate the dentist or technician from being required to create an impression or stone cast.

In a third embodiment, the dentist or technician can utilize a CT scan or series of CT scans for the basis of determining the appropriate position of the crown/PTF Assemblies 316 and the digitally parameterized fittings 152". The dentist or technician can use the CT scan data for determining or planning the position of the implant locations and ultimately the position of the digitally parameterized fittings 152". The use of a radiographic stent demonstrating the ideal tooth position for the restoration can also be included in this process and provide the dentist and technician with an ability to align the Crown/PTF Assemblies 316 relative to the contours of the radiographic stent or relative to the position of the opposing arch. The dentist or technician could also utilize a CT scan of the patient's previous existing dentition, which could be aligned utilizing anatomical markers, in order to determine the ideal position of the Crown/PTF Assemblies 316.

These alternate embodiments only demonstrate some of the potential options in combining different digital data acquisition protocols into the invented process. As can be appreciated, these are only a handful of potential embodiments of the invented process, but should provide insight as to the adaptation of future technologies.

What is claimed is:

1. A dental prosthesis and a plurality of implants and abutments to which the dental prosthesis mates, wherein the dental prosthesis comprises:
    a plurality of support posts, a plurality of crowns and a dental implant framework;
    where the position of the plurality of support posts and the plurality of crowns is determined from digital data defining the appropriate tooth position for the dental prosthesis;
    where the plurality of support posts and the plurality of crowns consist of predefined dimensions;
    a plurality of fittings to mate with the corresponding plurality of implants and abutments when inserted in the patient's mouth;
    where the position of the plurality of fittings has been determined through the use of digital data identifying the location of the plurality of implants and abutments in the patient's mouth;
    a bridging structure or plurality of bridging structures attaching the support posts and fittings to one another; and
    the combination of the bridging structure or plurality of bridging structures, plurality of support posts, and plurality of fittings providing the complete embodiment of the dental implant framework.

2. The dental prosthesis of claim 1, where the plurality of crowns are intended to intimately mate to the plurality of support posts of the dental implant framework.

3. The dental prosthesis of claim 2, wherein the design of the plurality of support posts is based upon at least one of the contours of each crown of the plurality of crowns and the contours of the tooth that each crown of the plurality of crowns is intended to replace.

4. The dental prosthesis of claim 2, where in the design of the plurality of support posts includes at least one of a planar margin where each crown of the plurality of crowns will mate and a non-planar margin where each crown of the plurality of crowns will mate.

5. The dental prosthesis of claim 2, wherein the design of each crown of the plurality of crowns is based upon at least one of the contours and dimensions of the tooth it is intended to replace, the contours of denture teeth and a standardized library of crown files.

6. The dental prosthesis of claim 2, where the plurality of crowns and plurality of support posts are fully parametric and easily edited during the design phase.

7. The dental prosthesis of claim 6, where each crown of the plurality of crowns have features, each support post of the plurality of support posts have features and where the features of each crown of the plurality of crowns and the features of each support post of the plurality of support posts are dependent upon one another; and this dependency allows for changes in orientation, dimensions or features in any one of the support posts of the plurality of the support posts or any one of the crowns of the plurality of crowns as a result of modifications to the associated support post or crown.

8. The dental prosthesis of claim 7, where each crown of the plurality of crowns include at least one of a separate CAD body for a coping, a separate CAD body for a cutback coping, a selectable feature to reduce each crown of the plurality of crowns body to a coping, and a selectable feature to reduce each crown of the plurality of crowns body to a cutback coping.

9. The dental prosthesis of claim 2, where the plurality of crowns are united to create a bridge.

10. The dental prosthesis of claim 9, where the bridge includes the gingiva contours captured from at least one of the digital data defining the appropriate tooth position for the final dental prosthesis and contours as designed by the operator.

11. The dental prosthesis of claim 2, where each crown of the plurality of crowns include the gingiva contours captured from at least one of the digital data defining the appropriate tooth position for the final dental prosthesis and contours as designed by the operator.

12. The dental prosthesis of claim 2, where the support posts of the plurality of support posts are united into a larger singular support post intended to support a bridge.

13. The dental prosthesis of claim 12, where the larger singular support post is modified in order to support a bridge.

14. The dental prosthesis of claim 1, where the plurality of crowns and dental implant framework can be manufactured simultaneously.

15. The dental prosthesis of claim 14, where each crown of the plurality of crowns is fabricated out of at least one of a metallic material, a ceramic material, an acrylic material, and a biocompatible material.

16. The dental prosthesis of claim 14, where the dental implant framework is fabricated out at least one of titanium or other metallic materials, Zirconia or other ceramic materials, acrylic or other composite materials, and a biocompatible material.

17. The dental prosthesis of claim 1, where in the digital data defining the appropriate tooth position is derived from at least one of scanning a diagnostic wax up or denture tooth set up, the alignment of tooth or crown CAD models in a virtual set up, the alignment of the plurality of support post and plurality of crown assemblies in a virtual set up, an intraoral scan of a diagnostic wax up or denture tooth set up taken in the patient's mouth, a CT scan or series of CT scans of the patient's mouth, and a CT scan or series of CT scans with the use of a radiographic stent in the patient's mouth.

18. The dental prosthesis of claim 1, where in the digital data for locations of the plurality of implants and abutments have been derived from at least one of scanning analogs in a stone cast of the patient, an intraoral scan of the plurality of implants and abutments in the patient's mouth, digital surgical planning of the proposed implant positions on the basis of a CT scan or series of CT scans, and a CT scan or series of CT scans.

19. The dental prosthesis of claim 1, where the gingiva structures of the prosthesis can be constructed out of at least one of acrylic and ceramic material.

20. A dental implant framework intended to mate with plurality of crowns and a plurality of implants and abutments comprising:

a plurality of support posts for supporting and mating with a plurality of crowns;

where the position of each of the support posts of the plurality of support posts is determined from digital data defining the appropriate tooth position for the dental prosthesis;

where each support post of the plurality of support posts consist of predefined dimensions;

a plurality of fittings to mate with the corresponding plurality of implants and abutments when in the patient's mouth;

where the position of each of the fittings of the plurality of fittings has been determined through the use of digital data identifying the location of the plurality of implants and abutments in the patient's mouth;

a bridging structure or plurality of bridging structures attaching the plurality of support posts and the plurality of fittings to one another; and the combination of the bridging structure or plurality of bridging structures, the plurality of support posts, and the plurality of fittings provides the complete embodiment of the dental implant framework.

21. The dental implant framework of claim 20, where in the digital data defining the appropriate tooth position is derived from at least one of scanning a diagnostic wax up or denture tooth set up, the alignment of tooth or crown CAD models in a virtual set up, the alignment of the plurality of support posts and the plurality of crowns in a virtual set up, an intraoral scan of a diagnostic wax up or denture tooth set up taken in the patient's mouth, a CT scan or series of CT scans of the patient's mouth, and a CT scan or series of CT scans with the use of a radiographic stent in the patient's mouth.

22. The dental implant framework of claim 20, wherein the design of each of the support posts of the plurality of support posts is based upon at least one of the contours of each of the crowns of the plurality of the crowns it is intended to mate to and the tooth that each crown of the plurality of crowns is intended to replace.

23. The dental implant framework of claim 20, where in the design of the plurality of support posts includes at least one of a planar margin where the plurality of crowns will mate and a non-planar margin where the plurality of crowns will mate.

24. The dental implant framework of claim 20, where the design of the framework is performed concurrently with the design of each crown of the plurality of crowns that are intended to mate with the framework.

25. The dental implant framework of claim 20, where each support post of the plurality of support posts are fully parametric and easily edited during the design phase.

26. The dental implant framework of claim 20, where in the digital data for locations of the plurality of implants and abutments have been derived from at least one of the scanning the analogs in the stone cast of the patient, an intraoral scan of the plurality of implants and abutments in the patient's mouth, digital surgical planning of the proposed implant positions on the basis of a CT scan or series of CT scans, and a CT scan or series of CT scans.

27. The dental implant framework of claim 20, where the dental implant framework is fabricated out of at least one of titanium or other metallic materials, zirconia or other ceramic materials, acrylic or other composite materials, and a biocompatible material.

28. A method for designing and fabricating a dental prosthesis comprising of a dental implant framework and a plurality of crowns intended to mate to a plurality of implants and abutments comprising:
providing digital data of the tooth orientation or to determine the tooth orientation for the dental prosthesis;
aligning each crown of the plurality of crowns and each support post of a plurality of support posts relative to the digital data of the tooth orientation or determined tooth orientation for the proposed final prosthesis;
providing digital data of the position of the plurality of implants and abutments in the patients mouth;
aligning a plurality of fittings relative to the digital data which captures the position of the plurality of implants and abutments in the patient's mouth;
utilizing bridging structures to attach the plurality of support posts and the plurality of fittings to one another;
combining the plurality of fittings, plurality of support posts, and bridging structures to define a final CAD model of the dental implant framework; and
exporting the CAD models of the framework and the plurality of crowns to be simultaneously manufactured.

29. The method of claim 28, where in the digital data defining the appropriate tooth position is derived from at least one of scanning a diagnostic wax up or denture tooth set up, the alignment of tooth or crown CAD models in a virtual set up, the alignment of each support post of the plurality of support posts and each crown of the plurality of crowns in a virtual set up, an intraoral scan of a diagnostic wax up or denture tooth set up taken in the patient's mouth, a CT scan or series of CT scans of the patient's mouth, and a CT scan or series of CT scans with the use of a radiographic stent in the patient's mouth.

30. The method of claim 29, where support post of the plurality of support posts and each crown of the plurality of crowns are imported from at least one of a CAD library of support posts and crowns, are imported and aligned together and are imported and aligned separately.

31. The method of claim 30, where in the design of each support post of the plurality of support posts is based upon at least one of the contours of each crown of the plurality of crowns and the tooth each crown of the plurality of crowns is intended to replace.

32. The method of claim 31, where in the design of each support post of the plurality of support posts includes at least one of a planar margin where the plurality of crowns will mate and a non-planar margin where the plurality of crowns will mate.

33. The method of claim 32, where the design of each crown of the plurality of crowns is based upon at least one of the contours and dimensions of the tooth it is intended to replace, the contours of denture teeth and standardized library of crown files.

34. The method of claim 33, where each crown of the plurality of crowns and each support post of the plurality of support posts are fully parametric and easily edited during the design phase.

35. The method of claim 34, where each crown of the plurality of crowns have features, each support post of the plurality of support posts have features and the features of the plurality of crowns and the features of the plurality of support posts are dependent upon one another; and
this dependency allows for changes in orientation, dimensions or features in any of the crowns of the plurality of crowns or any of the supports of the plurality of support posts will result in modifications to the second dependent body.

36. The method of claim 35, where the each crown of the plurality of crowns include at least one of a separate CAD body for a coping, a separate CAD body for a cutback coping, a selectable feature to reduce the body of each crown of the plurality of crowns to a coping and a selectable feature to reduce the body of each crown of the plurality of crowns to a cutback coping.

37. The method of claim 36, where the plurality of crowns are united to one another in creating a bridge.

38. The method of claim 37, where the gingiva contours captured in the digital data defining the appropriate tooth position for the final dental prosthesis are included from at least one of design of each crown of the plurality of crowns and in the design of each crown of the plurality of crowns as designated by the operator.

39. The method of claim 38, where in the digital data for locations of the plurality of implants and abutments have been derived from at least one of scanning the analogs in the stone cast of the patient, an intraoral scan of the plurality of implants and abutments in the patient's mouth, digital surgical planning of the proposed implant positions on the basis of a CT scan or series of CT scans, and a CT scan or series of CT scans.

40. The method of claim 39, where the gingiva structures of the prosthesis can be constructed out of at least one of acrylic and ceramic material.

41. The method of claim 40, where the plurality of crowns are fabricated out of at least one of a metallic material and a ceramic material.

42. The method of claim 41, where the dental implant framework is fabricated out of at least one of titanium or other metallic materials, zirconia or other ceramic materials, acrylic or other composite materials, and a biocompatible material.

* * * * *